US008968241B2

(12) United States Patent
Liversidge

(10) Patent No.: US 8,968,241 B2
(45) Date of Patent: Mar. 3, 2015

(54) MEDICAL NEEDLE SAFETY DEVICE

(76) Inventor: Barry Peter Liversidge, Langham (GB)

(*) Notice: Subject to any disclaimer, the term of this patent is extended or adjusted under 35 U.S.C. 154(b) by 0 days.

(21) Appl. No.: 13/576,323

(22) PCT Filed: Feb. 1, 2011

(86) PCT No.: PCT/GB2011/050159
§ 371 (c)(1),
(2), (4) Date: Aug. 24, 2012

(87) PCT Pub. No.: WO2011/092518
PCT Pub. Date: Aug. 4, 2011

(65) Prior Publication Data
US 2013/0006177 A1    Jan. 3, 2013

(30) Foreign Application Priority Data
Feb. 1, 2010   (GB) .................................. 1001506.3

(51) Int. Cl.
*A61M 5/32*   (2006.01)
*A61M 5/50*   (2006.01)
*A61M 5/00*   (2006.01)

(52) U.S. Cl.
CPC ............ *A61M 5/5086* (2013.01); *A61M 5/326* (2013.01); *A61M 2005/3247* (2013.01); *A61M 2005/3268* (2013.01)
USPC .......................... 604/111; 604/198; 604/263

(58) Field of Classification Search
CPC ............... A61M 2005/321; A61M 2005/3247; A61M 2005/3268; A61M 5/5086; A61M 5/3243; A61M 5/3202; A61M 5/321; A61M 5/3213; A61M 5/3271
USPC ......................................... 604/111, 198, 263
See application file for complete search history.

(56) References Cited

U.S. PATENT DOCUMENTS

2006/0211982 A1* 9/2006 Prestrelski et al. ............. 604/60
2008/0103453 A1* 5/2008 Liversidge .................... 604/187
(Continued)

FOREIGN PATENT DOCUMENTS

WO      2008067467       6/2008

OTHER PUBLICATIONS

International Search Report for PCT/GB2011/050159 dated Jul. 11, 2011.

*Primary Examiner* — Quynh-Nhu H Vu
(74) *Attorney, Agent, or Firm* — Andrus Intellectual Property Law, LLP

(57) ABSTRACT

A passive safety device for a medical needle has a mount for supporting the needle and a needle shielding sleeve co-axial with and arranged for sliding movement relative to the mount, from a shielding position to a non-shielding position. An abutment surface is provided on one of the sleeve and mount and is engageable by a radially deformable finger, when undeformed. A control member is also slidably arranged with respect to the mount and sleeve and has an initial set position. The control member co operates with the finger so that on sliding movement of the sleeve from its initial shielding position, the finger is moved radially outwardly, clear of the abutment surface and on to a sliding surface. Continued movement of the sleeve increases deformation of the finger and generates a restorative force between the finger and the sliding surface to move the sleeve back to a needle shielding position following the performance of a procedure and return the finger into radial alignment with the abutment surface, the control member remaining displaced from its set position.

17 Claims, 21 Drawing Sheets

(56) References Cited

U.S. PATENT DOCUMENTS

| | | | |
|---|---|---|---|
| 2008/0183140 A1* | 7/2008 | Paproski et al. | 604/232 |
| 2008/0249477 A1* | 10/2008 | Paproski et al. | 604/198 |
| 2009/0227956 A1* | 9/2009 | Emmott et al. | 604/196 |
| 2012/0310170 A1* | 12/2012 | Liversidge | 604/198 |
| 2013/0253444 A1* | 9/2013 | Liversidge | 604/263 |
| 2013/0296797 A1* | 11/2013 | Liversidge | 604/198 |

* cited by examiner

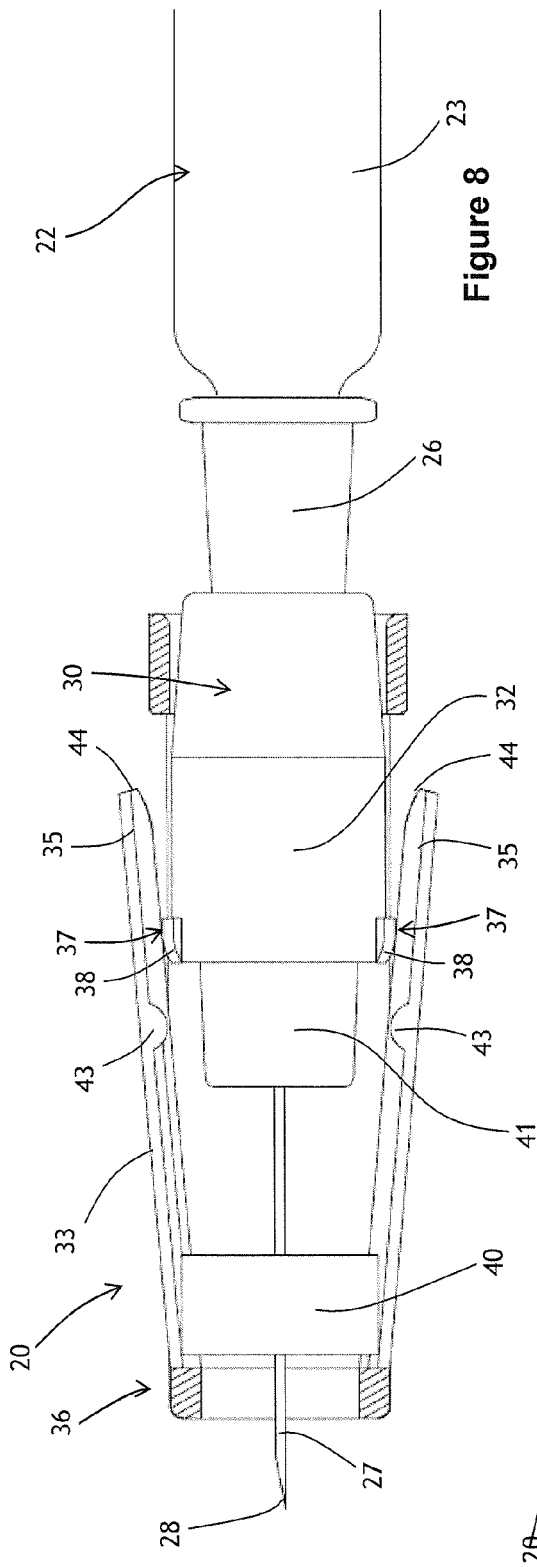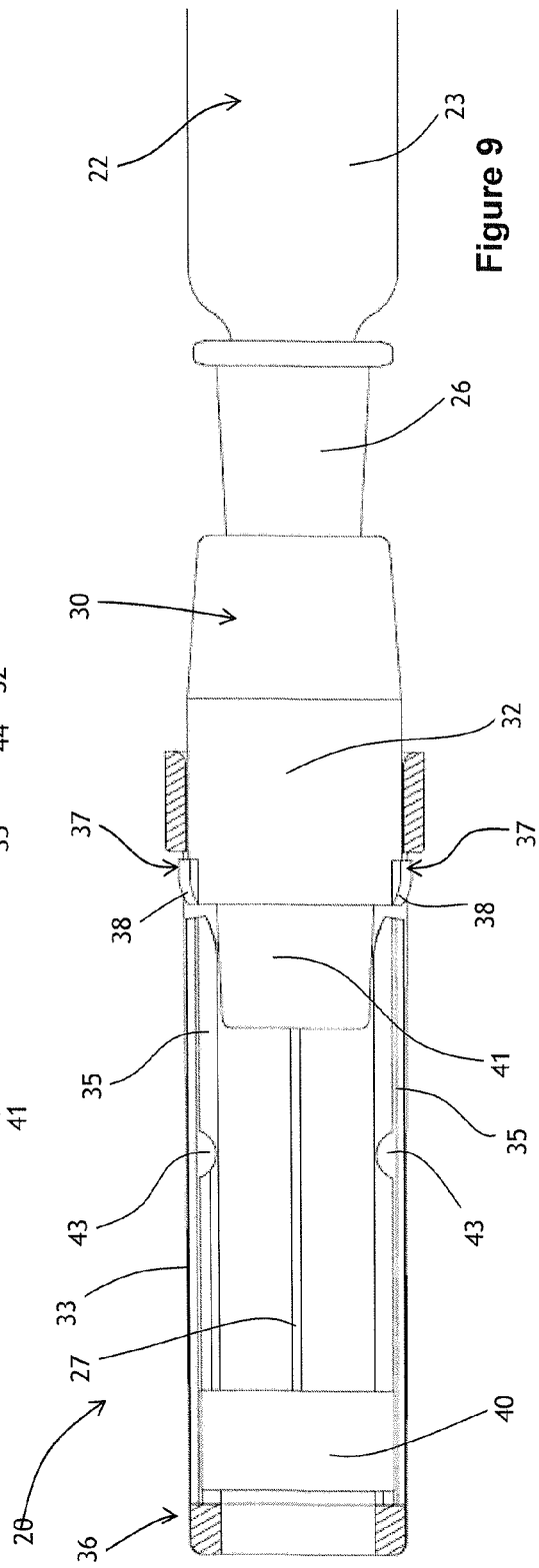

MEDICAL NEEDLE SAFETY DEVICE

CROSS REFERENCE TO RELATED APPLICATION

The present application is the U.S. national stage application of International Application PCT/GB2011/050159, filed Feb. 1, 2011, which international application was published on Aug. 4, 2011 as International Publication WO 2011/092518 A2. The Internation Application claims priority of British Patent Application 1001506.3, filed Feb. 1, 2010.

This invention relates to a safety device for use with a medical needle having a sharp tip, to confer passive protection to that needle. The invention also relates to a safety needle assembly including such a device and to an injection device incorporating such a safety needle assembly.

The safety device of this invention is intended for use with a medical needle used to penetrate a human or animal body, or for other medical uses such as the penetration of a pierceable membrane of an intravenous medication system. In the following all medical uses of the needle safety device will be described simply as the penetration of a body, even though specific embodiments may be intended for other medical uses.

Throughout this specification the terms "forward" and "forwardly" used in relation to the needle safety device and a syringe for use therewith refer to those ends of the components which are approached to a body when a procedure is to be performed, and the direction towards those ends. Conversely, the terms "rearward" and "rearwardly" refer to those ends of the components opposed to the forward ends and the direction away from those forward ends.

Fluids of various kinds may be administered to a body by means of a hollow needle in conjunction with a source of the required fluid. For example, such a needle may be associated with a syringe holding a liquid drug, the needle being used to penetrate the body at the site at which the drug is to be administered. Equally, body fluids may be withdrawn by using a hollow needle which is used to penetrate the body until the tip is located at the site from which fluid is to be withdrawn.

A recognised hazard for clinicians and other persons using or handling medical needles for the above described purposes is the risk of a so-called needle-stick injury—that is to say the accidental penetration of another's skin by the needle. Prior to the use of the needle to supply a fluid to or to withdraw fluid from a body, this rarely presents much of a problem, though once the needle has been used, there is a very much higher risk of a serious consequence for the clinician, or others associated with the disposal of a used needle. During use of the needle to penetrate the body tissues of a patient, the needle is likely to become contaminated with various organisms; should someone subsequently suffer a needle-stick injury, infection could occur.

There have been numerous proposals for protecting the sharp tip of a used needle, in order to reduce the risk of a needle-stick injury following use of the needle. Some proposals have actually increased the likelihood of such an injury by virtue of the action which must be performed to protect the tip, even if the risk thereafter is lessened. Despite all of the proposals which have previously been made, very few have achieved commercial success, nor has to there been wide acceptance by the medical industry. Many proposals are somewhat complex and involve a significantly greater manufacturing cost, and so are unacceptable on economic grounds. Others are much more difficult to use as compared to an unprotected needle, and so are rejected by clinicians. Yet further proposals do not allow compliance with best practice protocols.

A device which protects a needle tip after use without an operator having to perform any extra step on withdrawing the needle from a body is usually referred to as a passive protection device. This may be contrasted with an active protection device, where an operator is required to perform an extra step in order to protect a needle, following the withdrawal of the needle from a body. The requirement to perform an extra step leaves the needle unprotected for a longer period than with a passive protection device and further the performance of that extra step exposes the operator to a potentially hazardous situation, when needle-stick accidents can occur.

There is a significant demand for a passive protection device for use with a needle, and which allows a clinician or perhaps others to use the needle in much the same way as is done with an unprotected needle, but which can be manufactured economically and which provides a high degree of protection against needle-stick injury. In the case of health professionals, this demand is driven by health and safety legislation but in the case of others performing self-injections using a so-called pen injector, the used needles must be disposed of safely with minimum risk to others, even in the event that a sharps container is not immediately available. Further, particularly for self-injections, it is highly preferred that the device operates fully automatically, without intervention by the user, so as wholly to prevent access to the needle tip both before and after use, other than by a determined attempt to override the protection. In this way, protection may be afforded not just to the clinician or other user of the needle, but also to people who could come into a risky situation with used needles, such as waste disposal operators, cleaners, and so on.

The present invention has been developed with the aim of providing a simple, easy to use and economically viable safety device for a medical needle, to give passive protection thereto. In particular, the invention is concerned with a device which may be moulded from plastics materials and which does not require the use of metal springs. There is a particular problem with a plastic spring in that if the spring is stored in a stressed condition, there is a likelihood that the spring will lose at least some of its resilience and so may not be able to return to its as-manufactured unstressed condition. If this occurs, the passive operation of a device using a plastic spring may be unreliable.

It is a principal aim of this invention to provide a passive safety device for a medical needle which may incorporate a plastic spring and which is stored with the spring in a substantially unstressed condition such that when the device is required to give passive protection, it will operate effectively and reliably.

According to this invention, there is provided a safety device for shielding a medical needle having a sharp tip, which device comprises:

a needle mount for directly or indirectly supporting a medical needle;

a needle shielding sleeve for surrounding a supported needle and arranged coaxially with the mount so that a force applied to the sleeve slides the sleeve relative to the mount from a needle shielding position towards a non-shielding position whereat at least the tip of the needle is exposed beyond the sleeve;

an abutment surface and a sliding surface provided on one of the sleeve and mount;

a radially deformable resilient finger provided on the other of the sleeve and mount, and having a part in radial alignment with the abutment surface when the finger is undeformed to block movement of the sleeve from its needle shielding position;

a control member arranged coaxially with the sleeve and mount and slidably displaceable from a set position with respect thereto;

wherein movement of the sleeve towards a non-shielding position causes relative movement between the finger and the control member thus deforming the finger to move said part thereof out of radial alignment with the abutment surface and slidably displacing the control member from said set position to allow the sleeve to move to a non-shielding position and bring the finger into contact with the sliding surface, and continued movement of the sleeve slides the finger along the sliding surface to increase deformation of the finger and store energy in the finger for returning the sleeve to a needle shielding position whereat the finger is undeformed and said part is in radial alignment with the abutment surface, thereby to block movement of the sleeve towards a non-shielding position, consequent upon the displacement of the control member from the set position.

The medical needle may be essentially conventional and so have a hub carrying the needle itself, the hub being adapted for attachment to a source of a fluid to be injected, or a reservoir for fluid to be extracted from a patient. For convenience, in the following reference will be made solely to the injection of fluids and thus the source of fluid normally will comprise either a syringe, which may be pre-filled with medicament, or an injector into which a vial of medicament is inserted. In the case of a syringe, this may have any of the known connectors at the forward end thereof, to allow the needle hub to be attached thereto—for example, a Luer slip connector or a Luer lock connector. In the case of an injector, the needle hub may have a bore which is internally threaded, to allow the hub to be screwed on to the externally threaded boss at the forward end of an injector, the threading of the needle hub on to the injector causing the rear end of the needle to penetrate a bung associated with the vial so as thereafter to allow the dispensing of medicament through the needle.

Another possibility is for a syringe to have a needle permanently fitted thereto during manufacture. Such syringes are often pre-filled with medicament and are used to dispense a single dose of that medicament before being disposed of in a safe manner.

The term "needle mount" as used herein may extend to a needle hub carrying a needle as described above, or may comprise a separate component with which the needle hub is associated. In the case of a syringe having a needle permanently fitted thereto, the needle mount may comprise a formation at the forward end of the syringe and which directly carries the needle, the syringe barrel itself or a separate component which is fitted to that formation at the forward end of the syringe. Any of these arrangements are possible, so to long as the needle shielding sleeve is arranged for coaxial sliding movement with respect to the needle mount, which directly or indirectly (e.g. through a needle hub) supports the needle for use in a medical procedure. Then, force applied to the forward end of the sleeve when in its initial position (for example by being pressed against the skin at an injection site) slides the sleeve rearwardly relative to the mount, thereby exposing at least a part of the length of the needle, back from its sharp tip. Though exposed beyond the sleeve, in use the needle will actually have penetrated the injection site. The sleeve may slide over an outer surface of the mount, or internally within the mount, depending upon the particular configuration.

For convenience, the following description of preferred aspects of the invention will refer to a device having a single finger, but a practical embodiment of the device will have at least one, though typically two, three or even more, radially deformable resilient fingers each serving in effect as a leaf spring and circumferentially spaced around the component carrying the fingers. In a case where there are at least two fingers, both or all the fingers may be essentially the same. In the alternative, one finger may provide said part for engaging the abutment surface and another finger is arranged to slide on the sliding surface.

The finger may be provided on the sleeve and arranged for contact with either an abutment surface or a sliding surface on the mount. In the alternative, the finger may be provided on the mount, for contact with either an abutment surface or a sliding surface on the sleeve. The finger has an essentially undeformed condition (i.e. as moulded and so an unstressed condition) in which relative movement of the sleeve rearwardly with respect to the mount is blocked by the finger, unless said part of the finger has been moved out of alignment with the abutment surface, as will occur by the action of the control member in the first stage of the movement of the sleeve from its initial position.

Though in preferred embodiments the finger is moulded integrally with the component which carries the finger, and so with either the sleeve or the mount, it would be possible to manufacture the finger as a separate item which is then attached or otherwise associated with the component. This allows for different materials to be used for the component and the finger; for example it would be possible to make the finger as a leaf spring from a suitable metal.

When the finger is engaged with the sliding surface, rearward movement of the sleeve is possible with the finger sliding on the sliding surface. This resiliently deflects the finger outwardly in the generally radial direction, so storing energy in the finger. Then, on allowing the sleeve to move forwardly with respect to the mount (usually by moving the syringe, mount and needle rearwardly with respect to the injection site while the sleeve remains stationary engaged with that site), that stored energy serves to move the sleeve back to its shielding position. The resilient finger thus serves as a spring, urging the sleeve to its needle shielding position.

The control member preferably is provided within the greater diameter component (either the sleeve or the mount, depending on which component slides within the other), to deform the finger radially outwardly during an initial stage of rearward movement of the sleeve with respect to the mount towards a non-shielding position, so as to move said part of the finger out of alignment with the abutment surface and allow the finger to contact the sliding surface. Thereafter, continued rearward movement increases the deflection of the finger so storing more energy by the resilient deformation thereof.

The control member is initially located relative to the sleeve and mount at a set position with the finger adjacent or engaging the control member. Then, on initial rearward movement of the sleeve, the control member deforms the finger to move said part of the finger out of radial alignment with the abutment surface. Movement of the sleeve also causes displacement of the control member such that on subsequent return of the sleeve to a needle-shielding position, the control member is no longer located at said set position. If then an attempt is made to move the sleeve rearwardly, either deliberately or accidentally, said part of the finger will engage the abutment surface and block sleeve movement.

The finger may have one end mounted on either the sleeve or on the mount, said part of the finger being formed at or adjacent the other end thereof and being configured for engaging the abutment surface of the other component, when the finger is in its substantially undeformed condition. The abutment surface may comprise a shoulder formed on the other component, the shoulder being in the form of an annular surface between larger and smaller diameter parts of said other component.

In embodiments of this invention, the final needle shielding position of the sleeve, relative to the mount and when blocked against rearward movement, may be exactly the same as the initial needle shielding position thereof relative to the mount, or may differ slightly from that initial position. It may be advantageous in some embodiments to allow the sleeve to have a small degree of freedom of movement in the axial direction when in its shielding position, to assure proper operation of the safety device. In such a case, the initial position of the sleeve could be towards or at one extreme of that freedom of movement and the final position towards or at the other extreme of that freedom of movement. Despite this possible variation in the initial and final positions of the sleeve, the final position will be substantially the same as the initial position and functionally will be the same, in that in both positions the needle is shielded by the sleeve. Thus, it will be appreciated that the initial shielding position of the sleeve and the further shielding position thereof may in fact be the same axial position.

Before use of the device of any of the embodiments, it is important that there is a sufficient clearance between said part of the finger which engages the abutment surface and the abutment surface itself, to allow enough relative movement between the finger and the control member so that said part of the finger is moved by the control member radially clear of the abutment surface during initial movement of the sleeve. On return of the sleeve to its final shielding position, there will still be clearance between said part of the finger and the abutment surface when the sleeve is fully forward, but if an attempt is made to move the sleeve rearwardly, the finger will not be moved radially by the control member, as the control member no longer is at its set position. Thus, blocking of the sleeve will take place by the action of said part of the finger co-operating with the abutment surface.

The control member may serve as an indicator to show whether the device is ready for use or has been used and the sleeve is blocked against sliding movement with respect to the mount. To enhance this, the control member may be of a colour which contrasts with that of the sleeve and mount. A window may be provided in the coaxial arrangement of sleeve and mount within which the control member is slidably carried, said window being at the axial position to which the control member is moved when the sleeve is in its non-shielding position, whereby the control member may be observed through that window. Another possibility is for at least one of the coaxial arrangement of sleeve and mount to be of a translucent material whereby the position of the control member therewithin may be observed.

This invention extends to a safety needle device of this invention as discussed above in combination with a medical needle projecting forwardly from the needle mount, and also to an injection device fitted with the combination of the safety device and a medical needle.

By way of example only, certain specific embodiments of this invention will now be described in detail, reference being made to the accompanying drawings in which:—

FIG. 8 is similar to FIG. 7 but showing the returning movement of the sleeve;

FIG. 9 shows the sleeve returned to and blocked in a needle shielding position;

Figure 16:
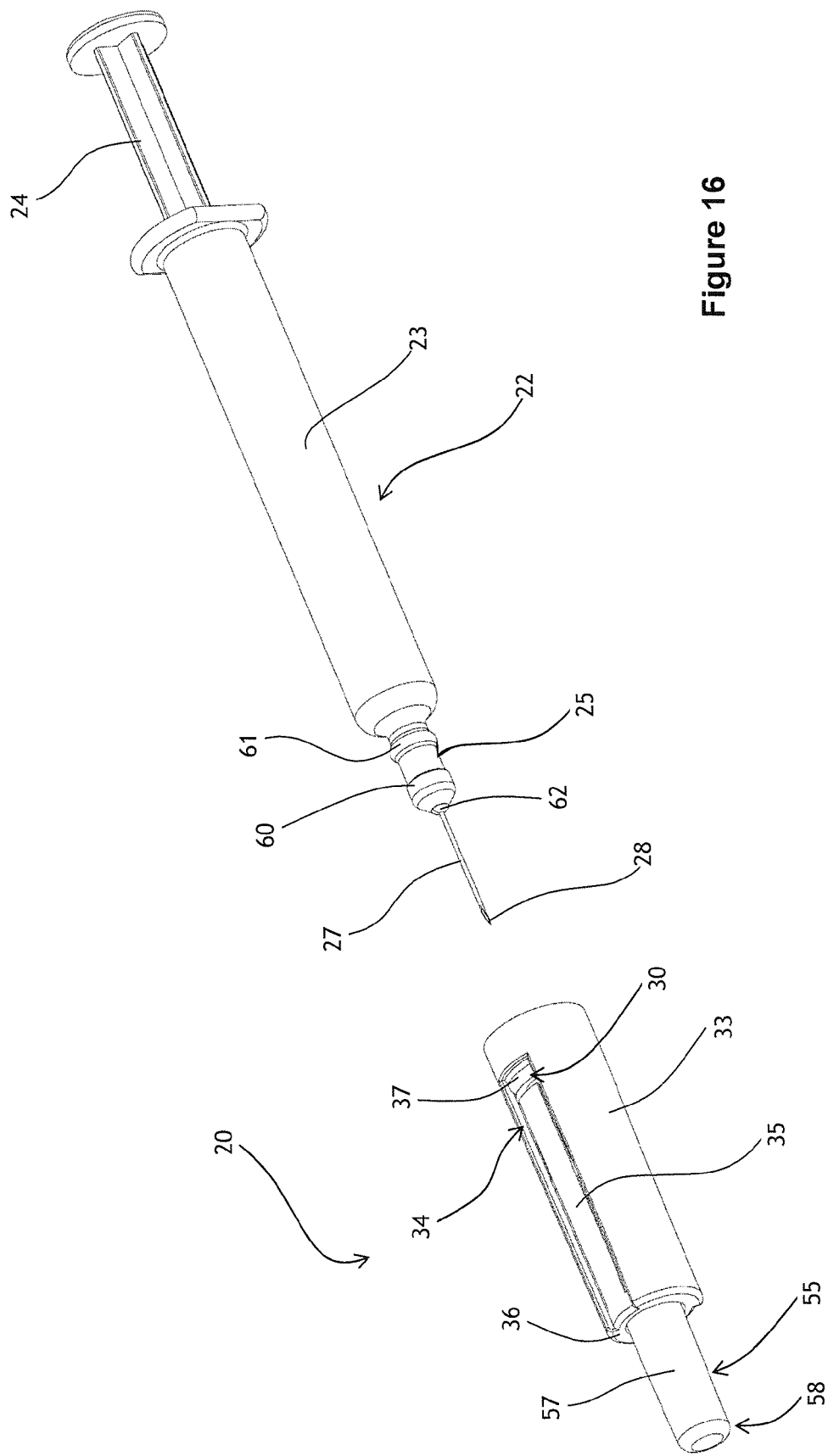
FIGS. 16, 17 and 18 show the first embodiment of device but with the needle fitted with a needle cover, FIG. 16 showing the device ready to be fitted to a syringe, FIG. 17 with the device fitted and ready for use, and FIG. 18 with the needle cover removed.
Figure 17:
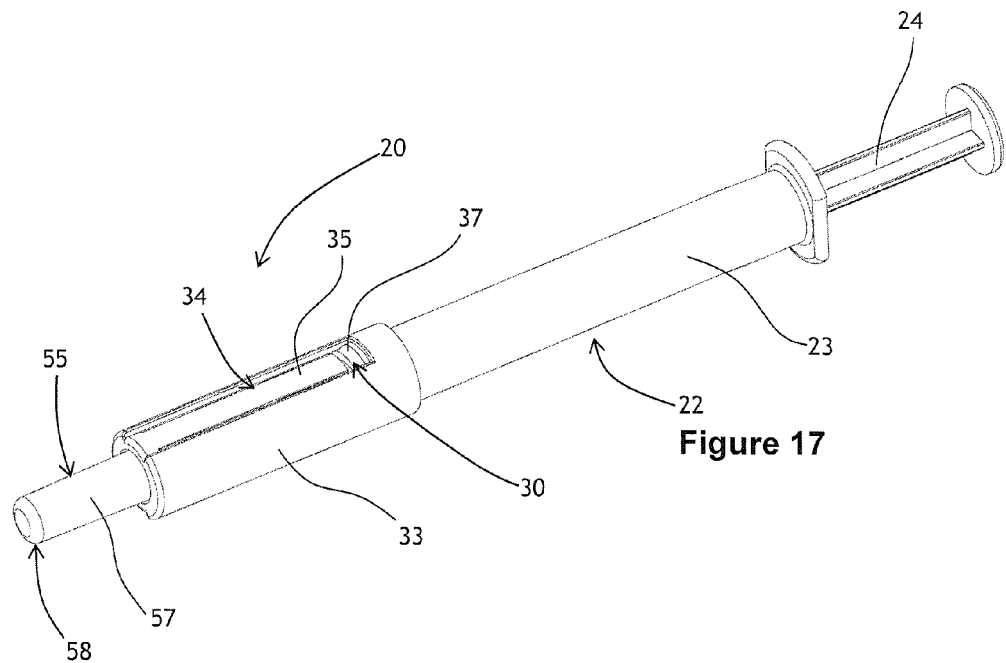
Figure 18:
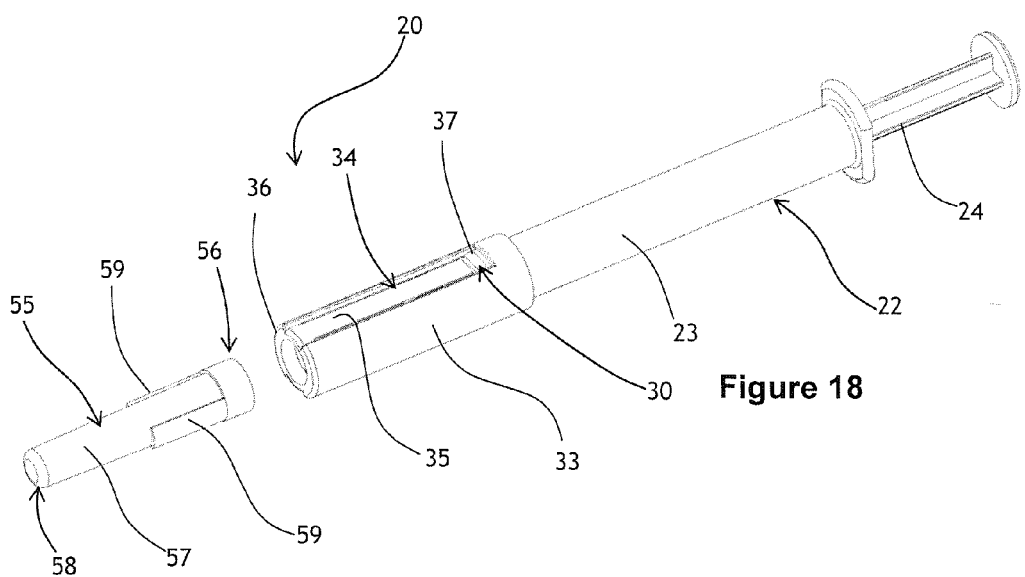
Figure 19:
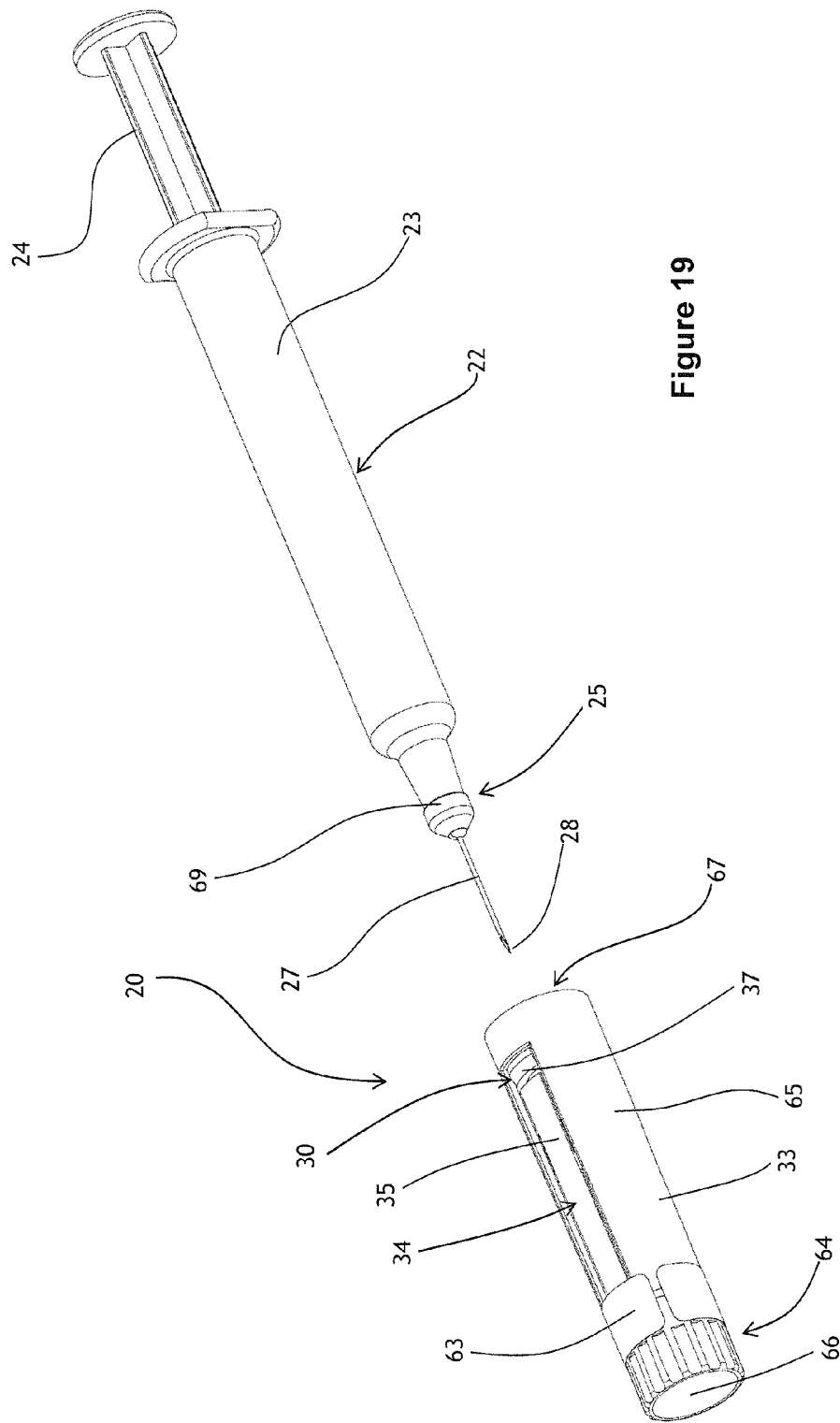
Figure 20:
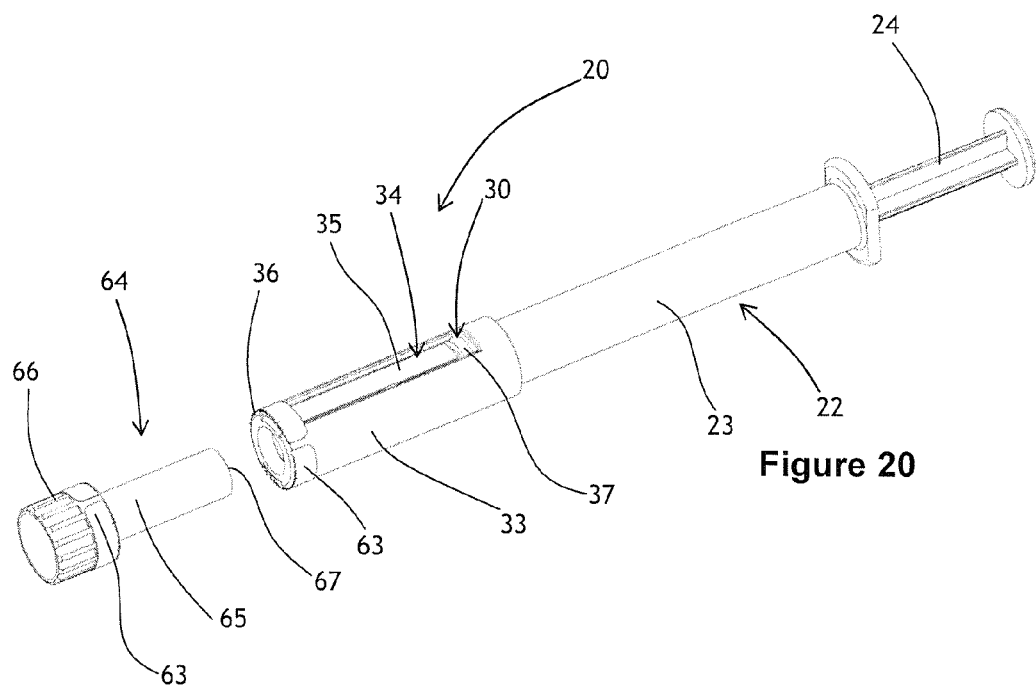
Figure 21:
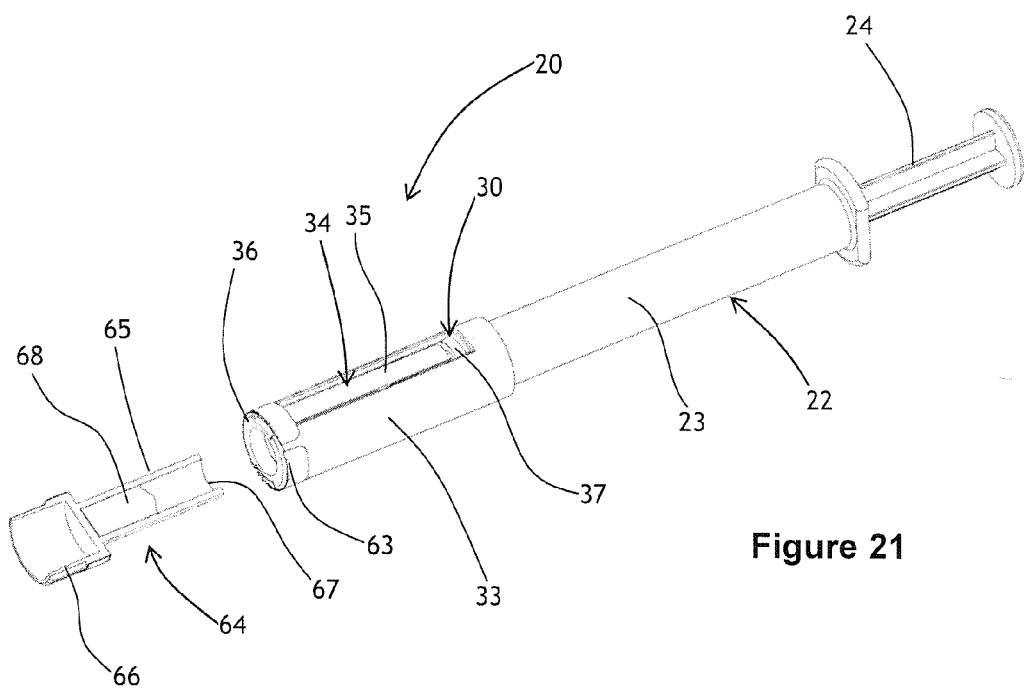
Figure 22:
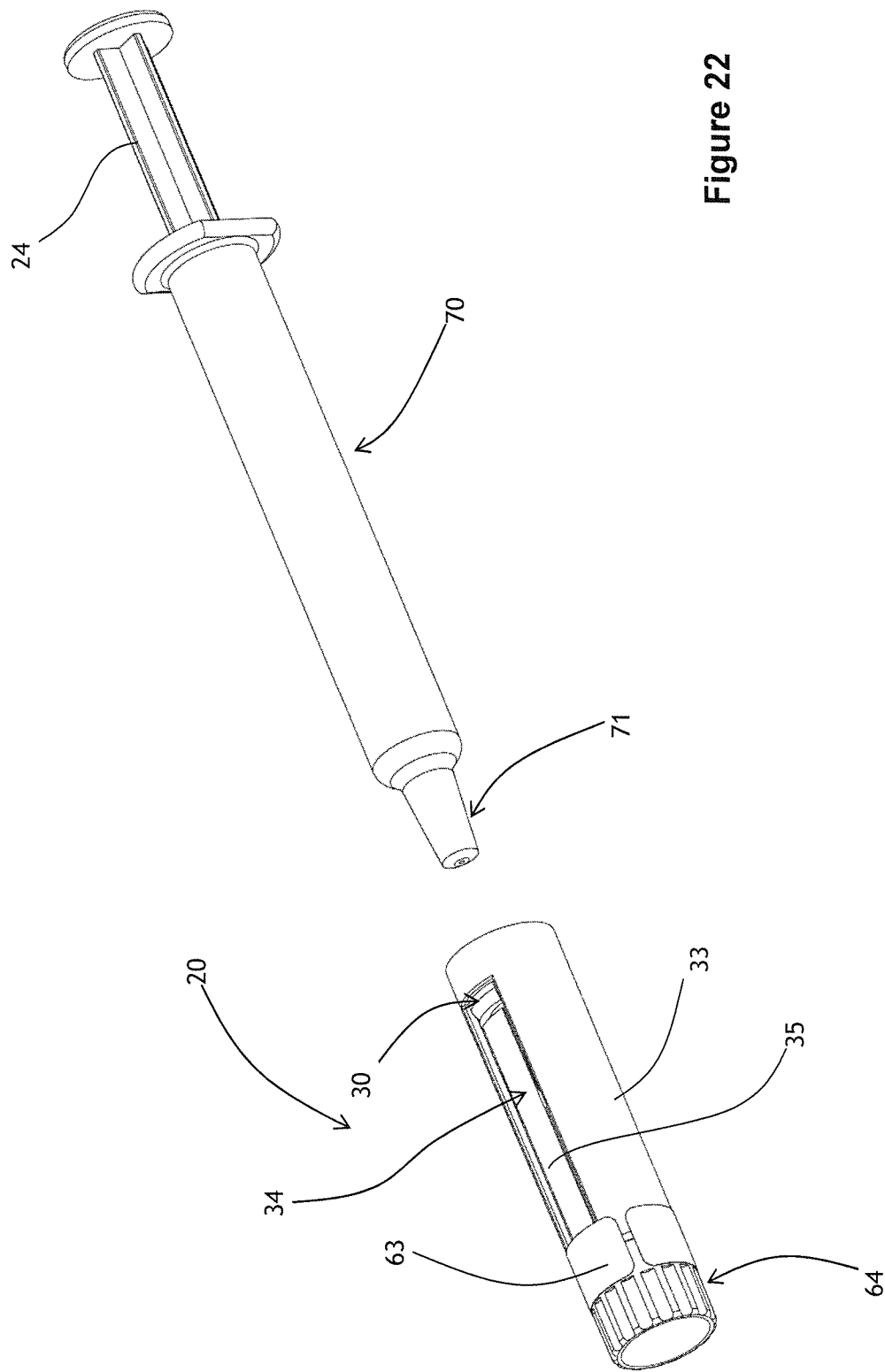
Figure 23:
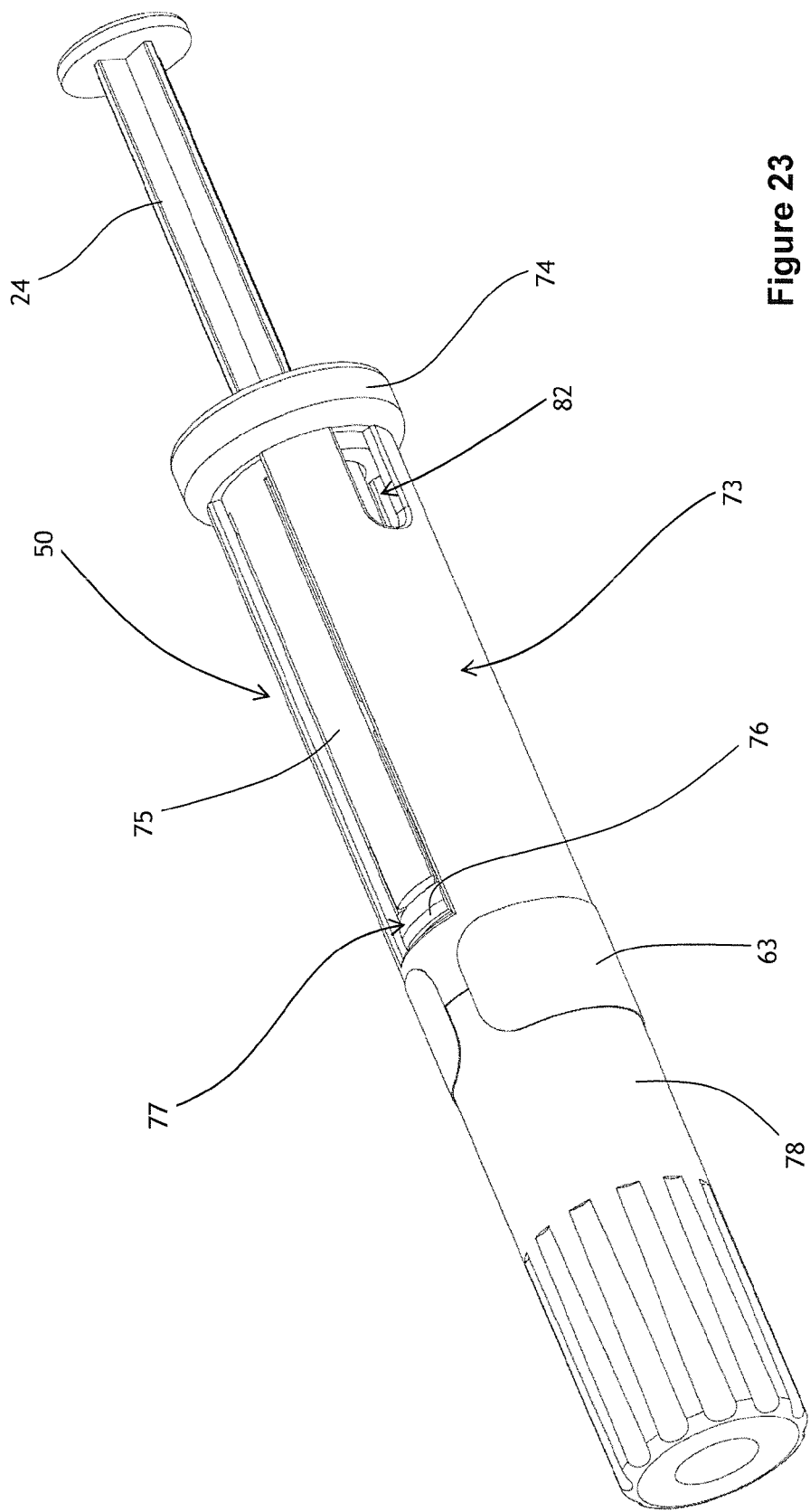
Figure 24:
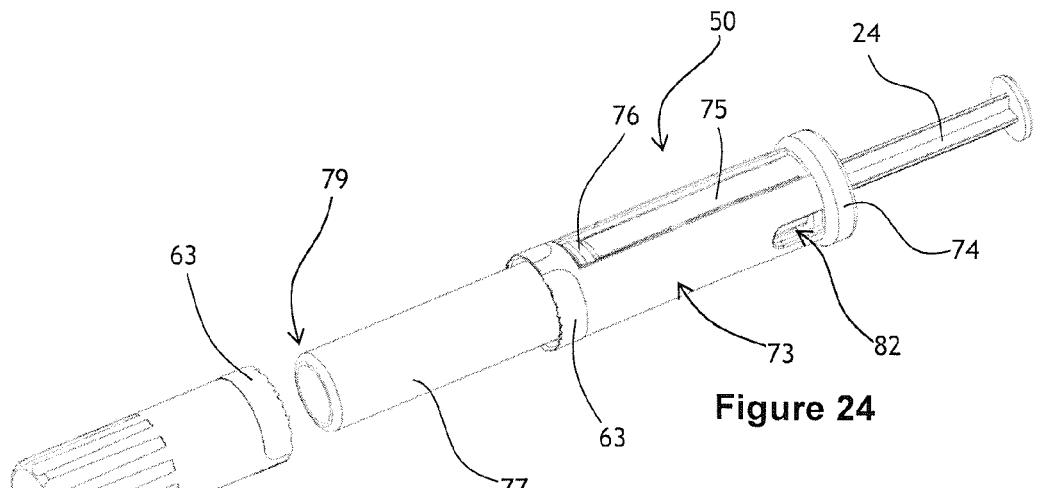
Figure 25:
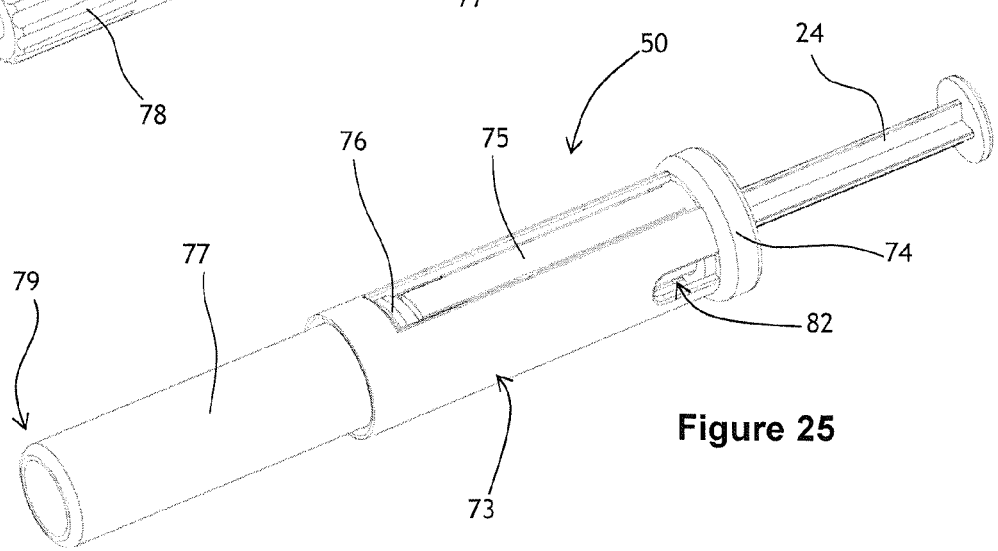
Figure 26:
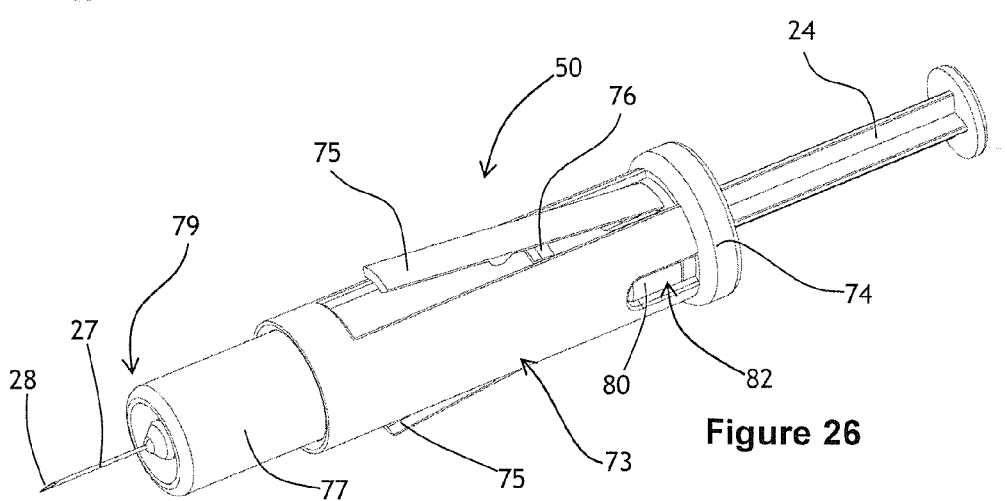
Figure 27:
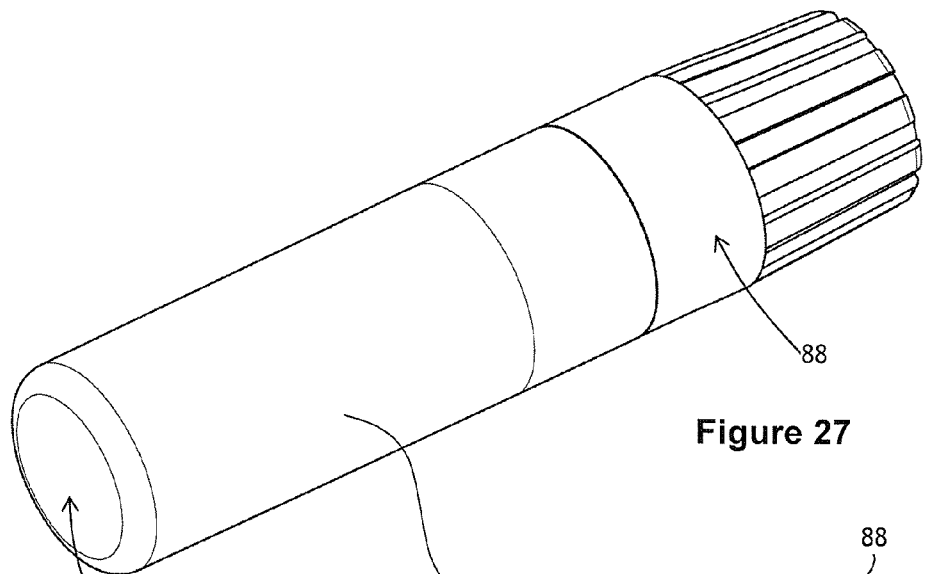
Figure 28:
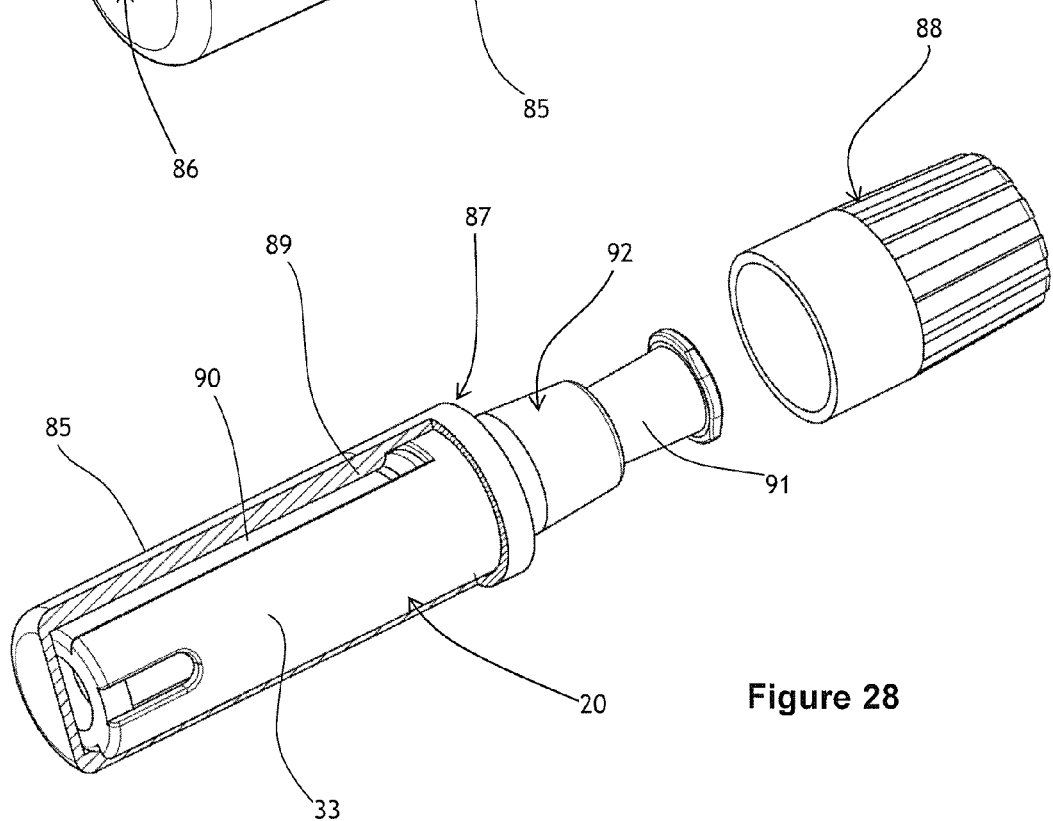
Figure 29:
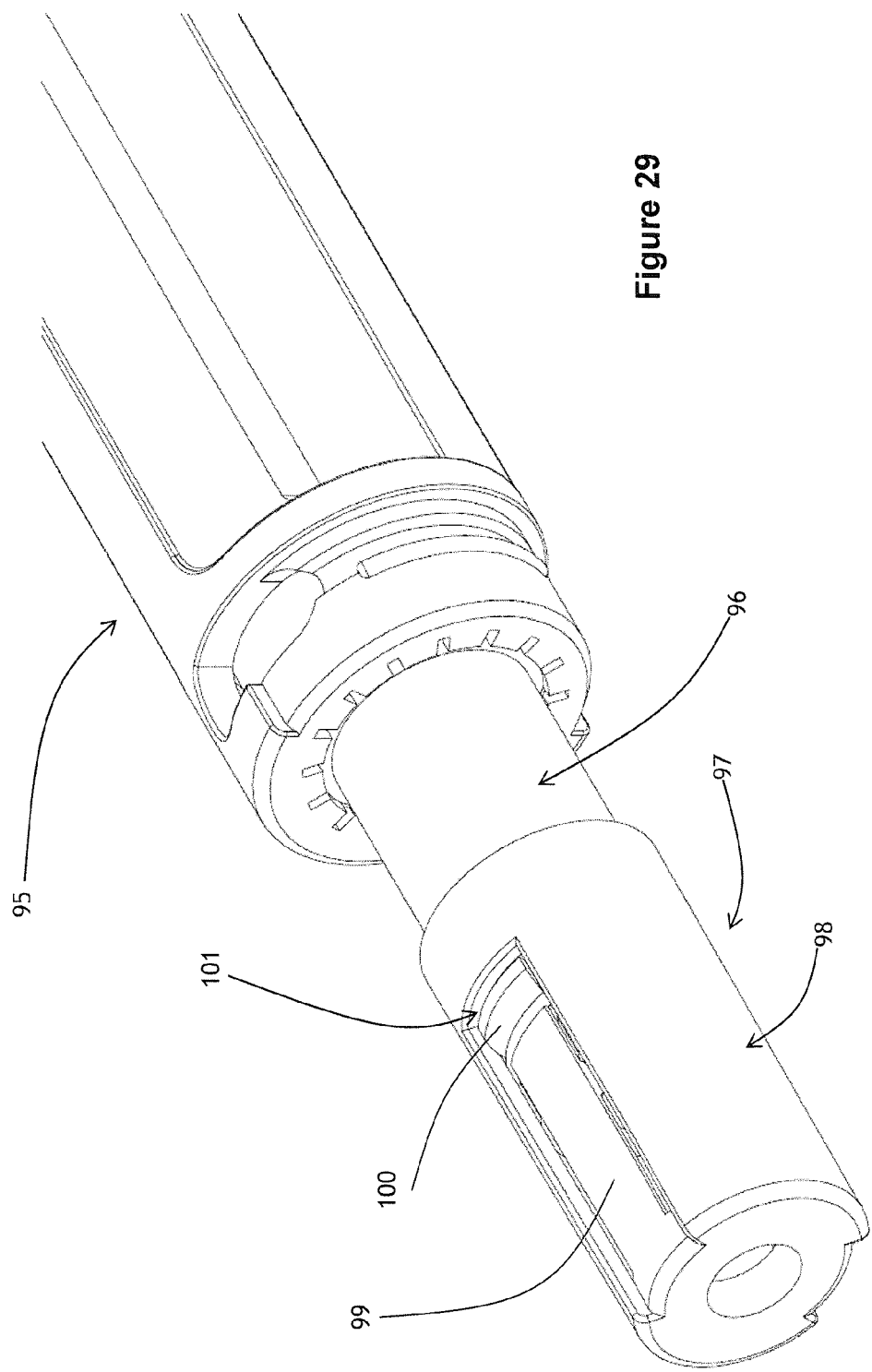

FIGS. 19, 20 and 21 also show the first embodiment of device again fitted with a needle cover but of a different design from that shown in FIGS. 16 to 18;

FIG. 22 shows an arrangement similar to that of FIGS. 19 to 21 but with a syringe not having a staked-in needle;

FIGS. 23 to 26 show a device similar to that of the second embodiment but arranged as a separate package for fitting to a pre-filled syringe with staked-in needle, FIG. 23 showing the package fitted to a syringe, FIG. 24 showing the package opened, FIG. 25 showing the assembly of the device and syringe ready for use and FIG. 26 showing the assembly with the sleeve withdrawn so exposing the needle;

FIGS. 27 and 28 show the device arranged as a self-contained package including a needle, ready for fitting to a syringe;

FIG. 29 is another embodiment of the safety device of this invention, being a modified form of the first embodiment and suitable for use with a pen injector; and FIGS. 30 and 31 and FIGS. 32 and 33 are two alternative indicator arrangements for the first embodiment.

Throughout the following description of the preferred embodiments of safety device of this invention, the same reference characters are used to identify corresponding parts of the various embodiments. Only the first embodiment will be described in complete detail and for a full understanding of other embodiments, reference may be made to the description of the first embodiment.

Referring initially to FIGS. 1 to 10 there is shown a first embodiment of safety device 20 arranged for shielding a medical needle 21 of a conventional form, intended for securing to a conventional syringe 22. The syringe has a cylindrical body 23 defining a cylindrical chamber for a liquid medicament, there being a plunger 24 fitted with a piston (not shown) at its forward end to expel medicament out of the nose 25 of the syringe. That nose has an external surface formed as a conventional Luer slip taper, for the connection thereto of a needle having a hub 26 with an internal Luer slip taper. The needle 27 is permanently bonded into the hub 26 and has a sharp tip 28. This arrangement is all entirely conventional and will not be described in further detail here.

Figure 3:
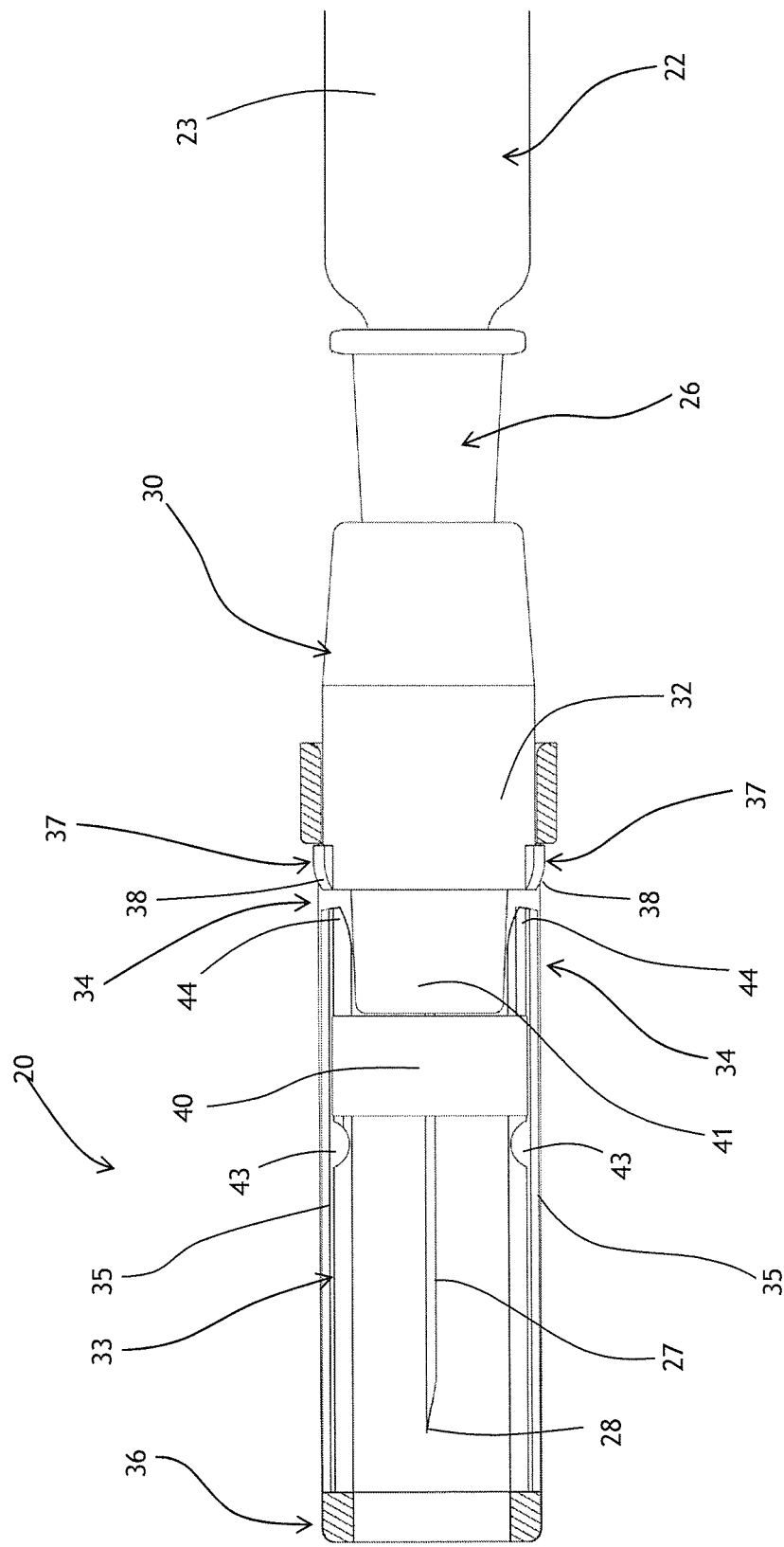
FIG. 3 is a cross-section through the device, in its initial setting with the sleeve in its shielding position.

The safety device 20 has a mount 30 provided with a bore which is adapted to be a close push-fit on ribbed section 31 of the needle hub 26, possibly slightly deforming the ribs to ensure there is sufficient friction between the hub and the mount. The mount has a cylindrical sliding surface 32 on which is supported a sleeve 33 arranged for axial sliding movement with respect to the mount and so also with respect to the needle. The initial needle-shielding position is shown in FIG. 3, and the sleeve may slide rearwardly to a non-shielding position shown in FIG. 7, where part of the needle back from its sharp tip 28 is exposed, so that a medical procedure may be performed. The sliding movement of the sleeve may take place as a part of that procedure, such as performing an injection.

The sleeve has a pair of opposed elongate apertures 34 within which are formed respective fingers 35 connected to the main part of the sleeve at the forward end 36 thereof, for serving as leaf springs. Though two such apertures each having a respective finger are shown, other numbers of apertures of fingers could be employed, ranging from a single aperture and finger up to three or four apertures and fingers and perhaps even five or more. Each finger 35 is resiliently deformable radially outwardly, as will be apparent from the following description of the device.

The mount 30 includes a pair of opposed lugs 37 formed at the forward end of the sliding surface 32 of the mount, which lugs locate in the apertures 34 of the sleeve and serve to prevent removal of the sleeve from the mount, once fitted thereon and the sleeve is in its initial position shown in FIG. 3. The forwardly directed surface 38 of each lug is of arcuate form, so as to facilitate fitting of the sleeve to the mount and also to provide a sliding surface for the associated finger, when the sleeve slides with respect to the mount.

A control member 40 is disposed within the sleeve 33 and in the initial setting of the device is disposed against a boss 41 formed at the forward end of the mount 30. The control member has a sufficiently large bore 42 for the needle 27 to pass easily therethrough during assembly but the bore is smaller than the diameter of the boss 41 such that the control member will bear on that boss 41 as the sleeve moves rearwardly, in the course of a procedure. Each finger 35 is formed with an opposed pair of inwardly directed protrusions 43 engageable with the external surface of the control member and disposed closely adjacent the control member in the initial setting of the device as shown in FIG. 3. Each finger has a central rib which runs on the sliding surface 38 of the mount as the sleeve moves rearwardly with respect thereto. The rearward end 44 of each finger is formed for engagement with the shoulder 45 between the sliding surface 32 and boss 41 of the mount when the finger is in an unstressed condition at the initial setting of the device. As shown in the drawings, the free end of each finger may be raked slightly and the shoulder 45 may be dished such that on the rearward end 44 of the finger engaging the shoulder, the finger is encouraged to move deeper into engagement.

At the forward end 36 of the sleeve, there are formed two diametrically-opposed windows 46, on a line perpendicular to that extending between the fingers 35. When the sleeve has moved fully rearwardly, so that the control member has been pushed to the forward end 36 of the sleeve, the control member will be visible through those windows 46 so as to serve as an indicator that the device has been used and now has the sleeve locked in the shielding position. This indication may be enhanced by making the control member of a brightly coloured material contrasting with the material of the sleeve.

In this embodiment, each of the mount, sleeve and control member is made of moulded plastics material. The fingers 35 are resiliently deformable radially outwardly by flexing of those fingers but in the initial position shown in FIG. 3, the fingers are in an undeformed (or unstressed) condition. Thus, the device may be stored in that condition without the fingers suffering from a loss of resilience, which otherwise would occur through storage when stressed.

Figure 1:
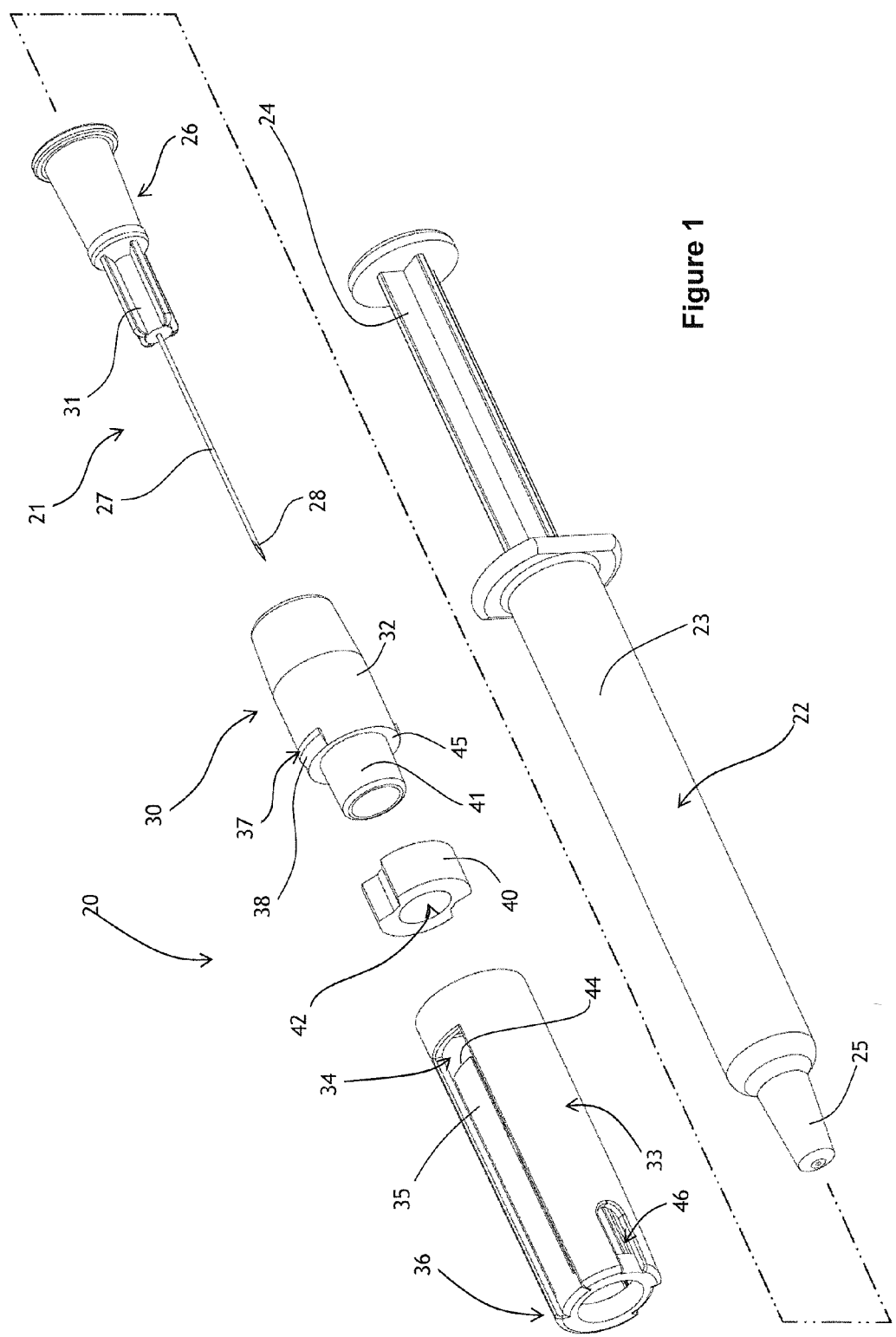
FIG. 1 is a diagrammatic isometric view of a syringe and a first embodiment of safety device of this invention, with the device shown in an exploded form.
Figure 2:
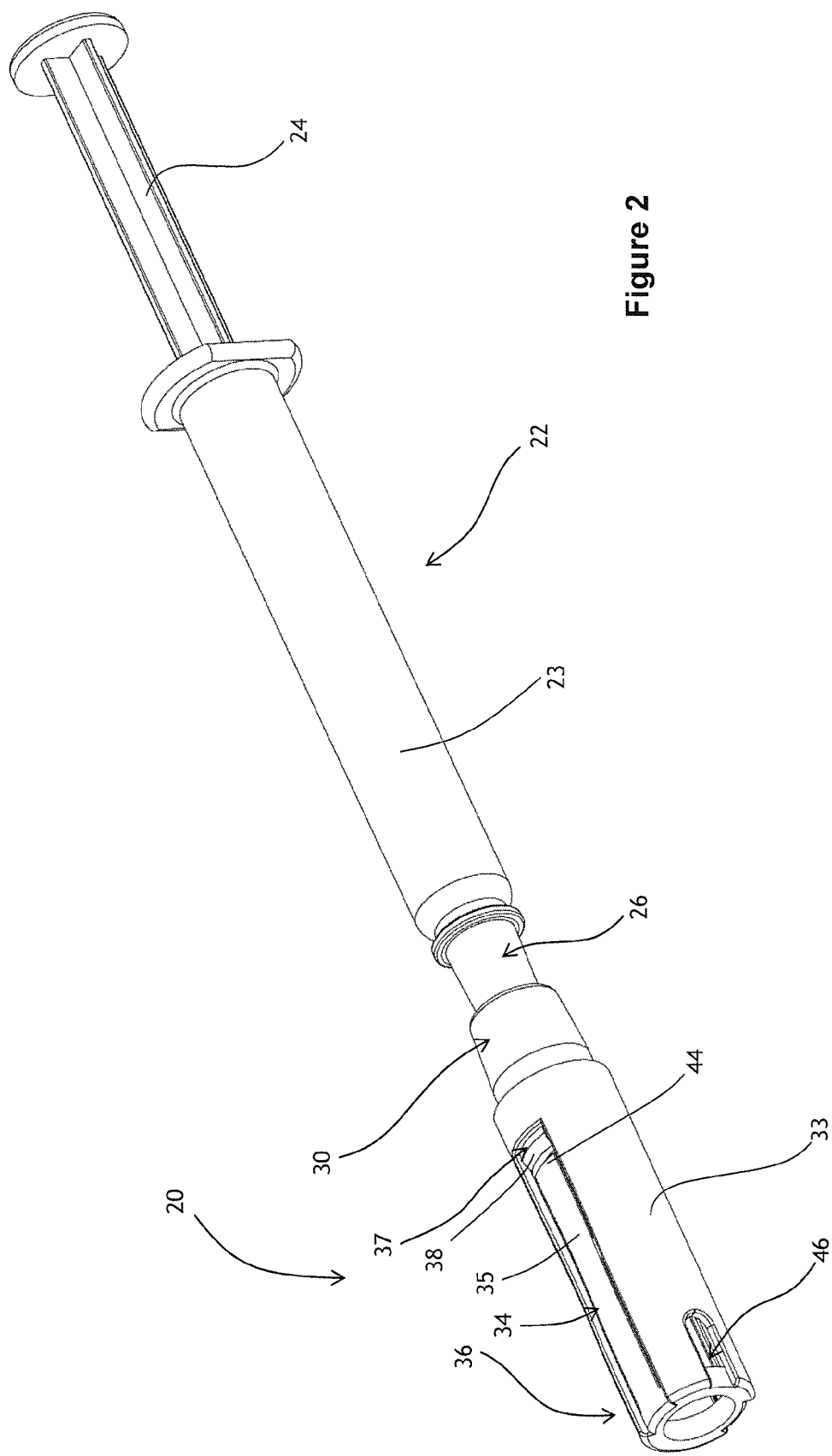
FIG. 2 is similar to FIG. 1 but with the device assembled and mounted on the syringe.

The operation of the safety device 20 described above will now be explained, following the fitting of the device to a needle 21. This action may be performed either before or after the needle hub 26 has been fitted to the Luer slip connector at the forward end of the syringe 22. The initial setting of the device is shown in FIGS. 2 and 3, with the sleeve 33 in its forward shielding position with respect to the needle so as to confer protection thereto. In this setting, the fingers 35 extend substantially parallel to the axis of the sleeve and mount and are in an undeformed as-moulded condition, as mentioned above. The control member 40 is disposed adjacent the boss 41 with the protrusions 43 of the fingers 35 adjacent the forward face of the control member. The sleeve is held against forward movement with respect to the mount 30 by virtue of the engagement of the rear end of each aperture 34 with the respective lugs 37.

Figure 4:
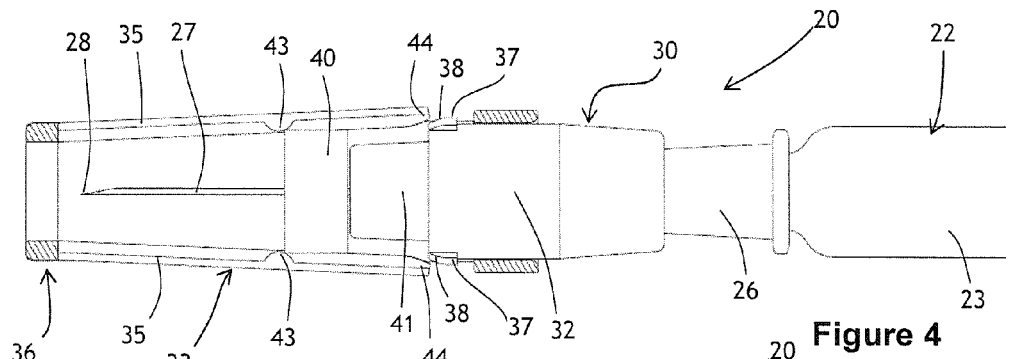
FIGS. 4 to 7 are similar to FIG. 3 but showing movement of the sleeve from the position of FIG. 3, sequentially to the sleeve being moved fully to its non-shielding position (FIG. 7)
Figure 5:
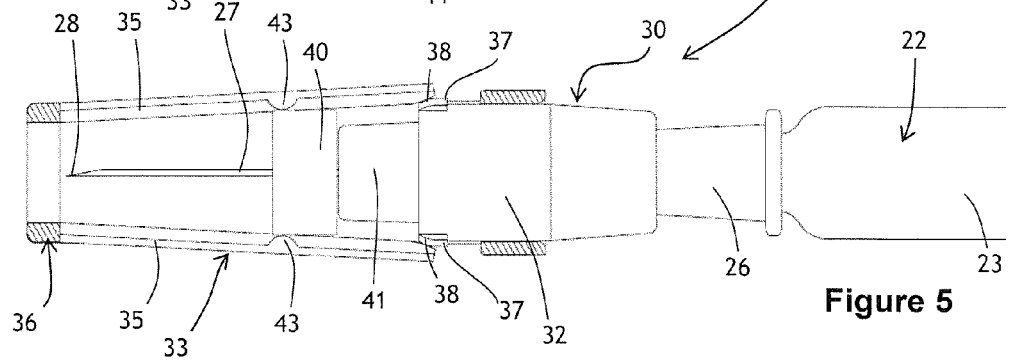
Figure 6:
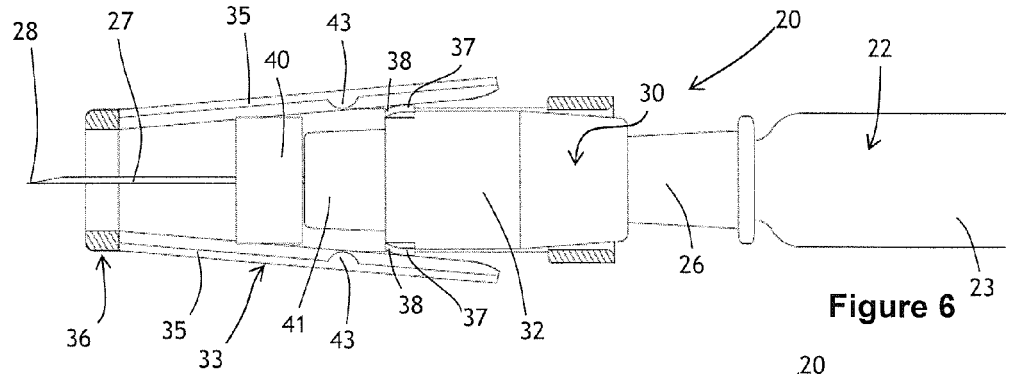
Figure 7:
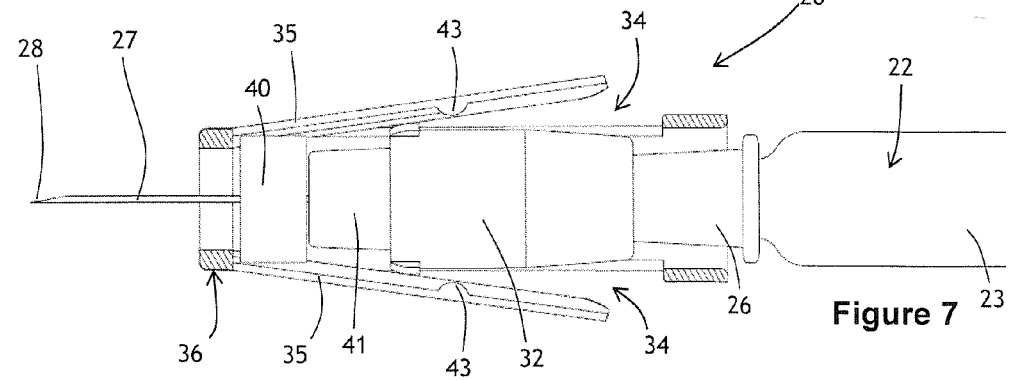
Figure 10:
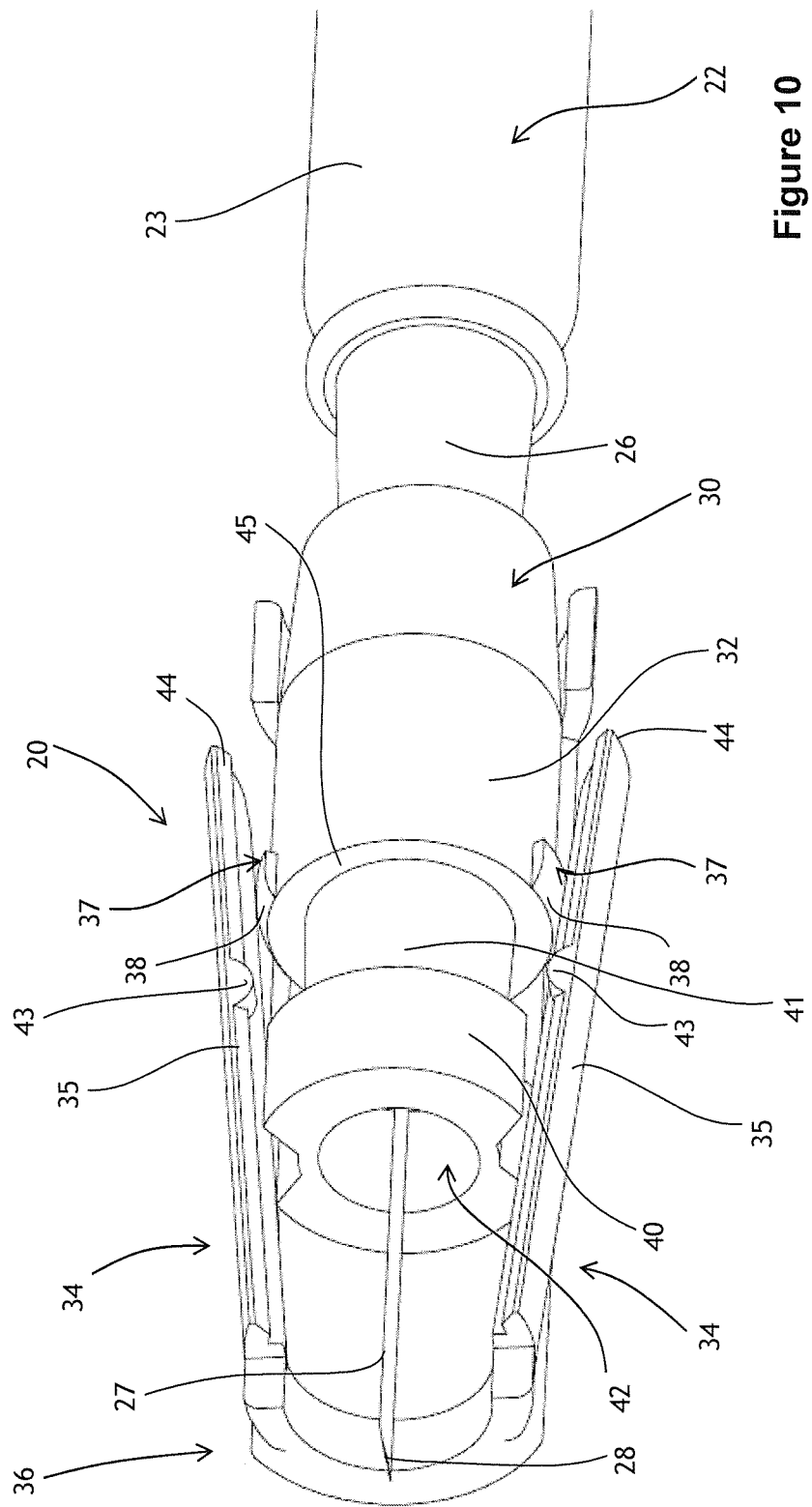
FIG. 10 is a cut-away isometric view of the safety device in a position corresponding to that of FIG. 6.
Figure 11:
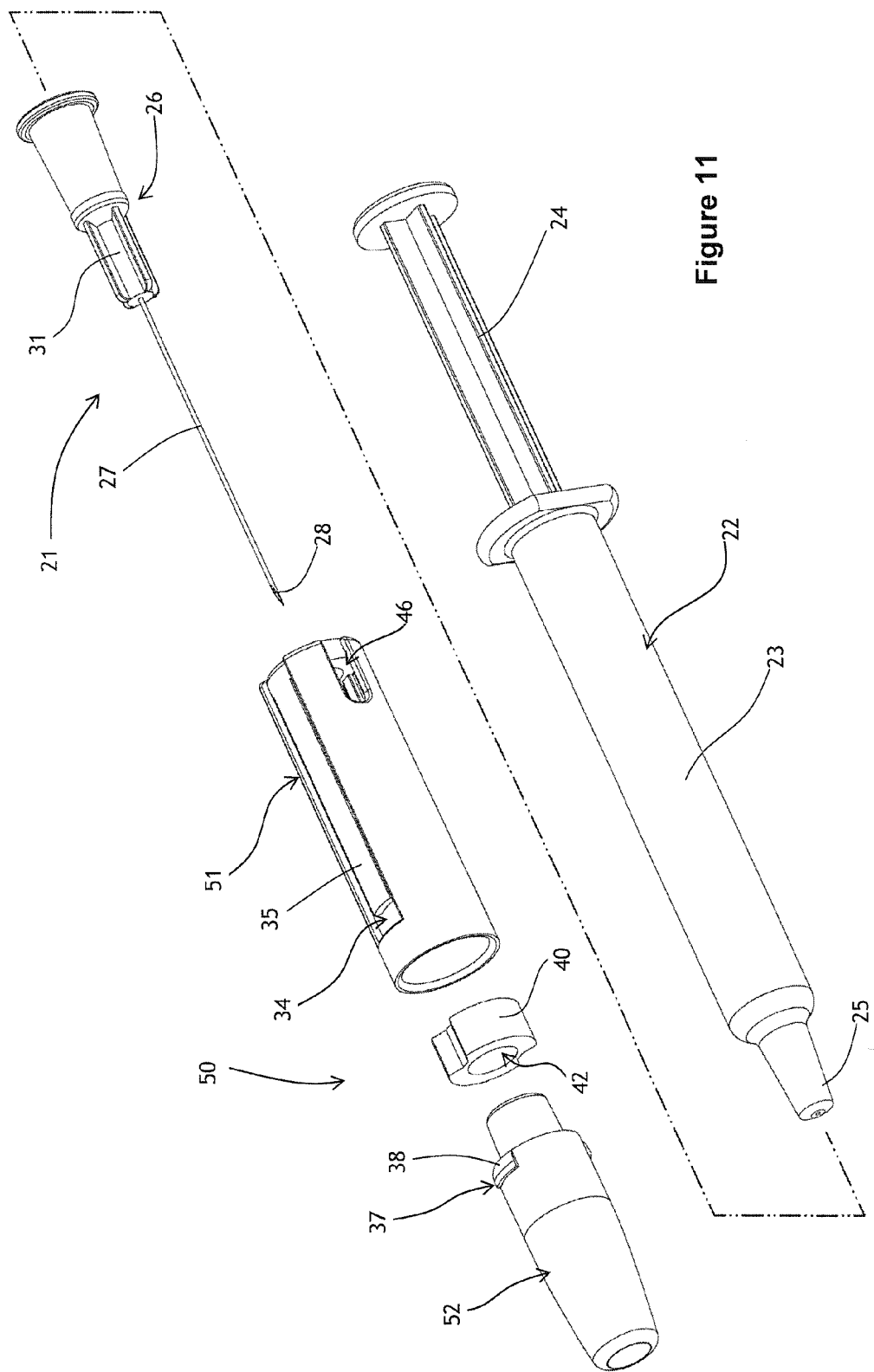
FIG. 11 is a diagrammatic isometric view of a syringe and a second embodiment of safety device of this invention, with the device shown in an exploded form.
Figure 12:
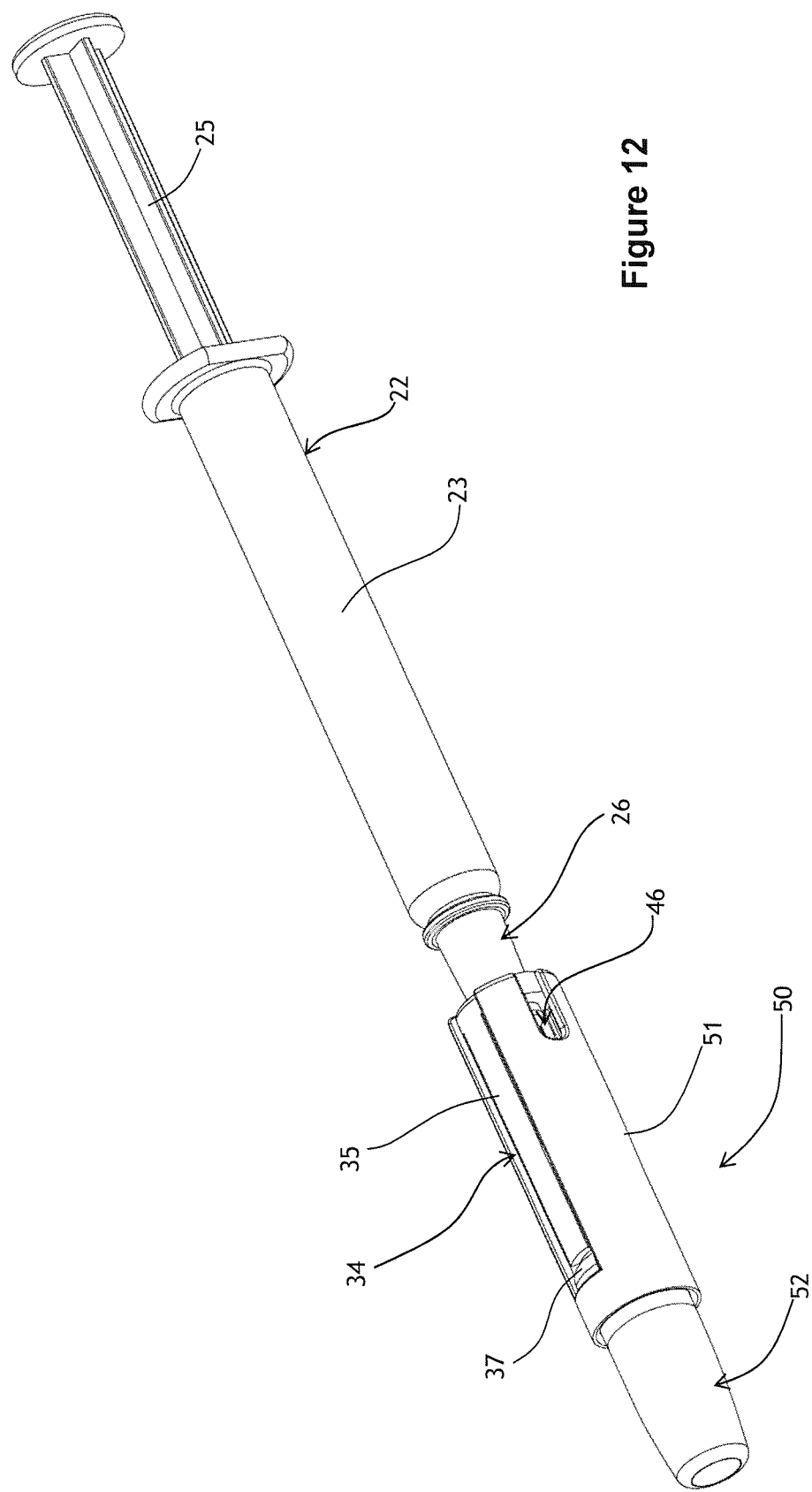
FIG. 12 is similar to FIG. 11 but with the device assembled and mounted on the syringe.
Figure 13:
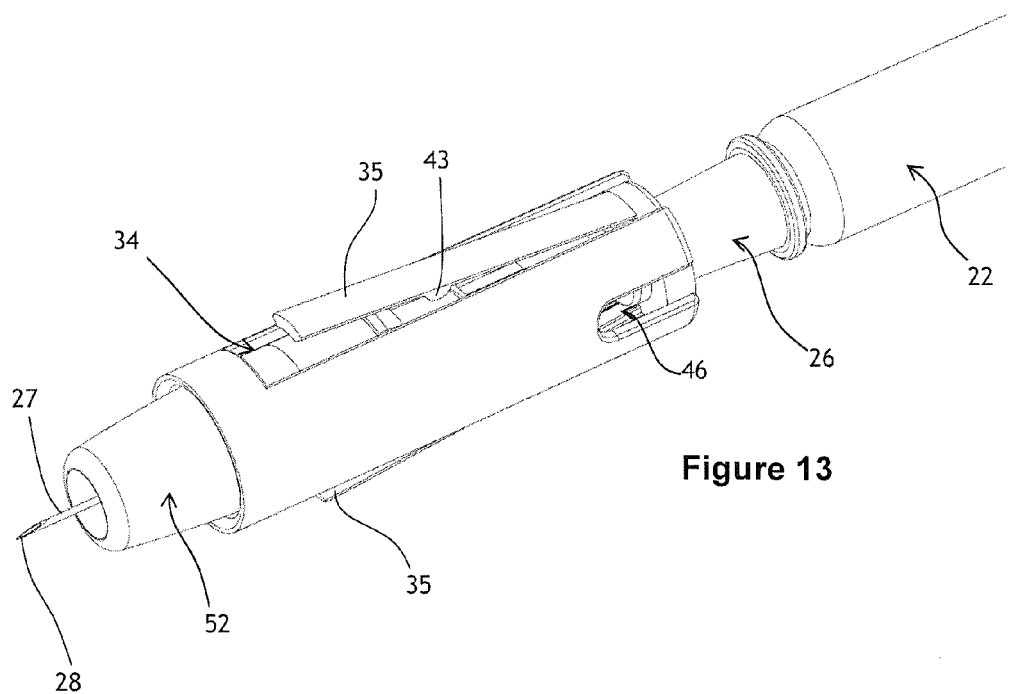
FIGS. 13 and 14 show two successive steps of the movement of the sleeve from its initial shielding position to its non-shielding position.
Figure 14:
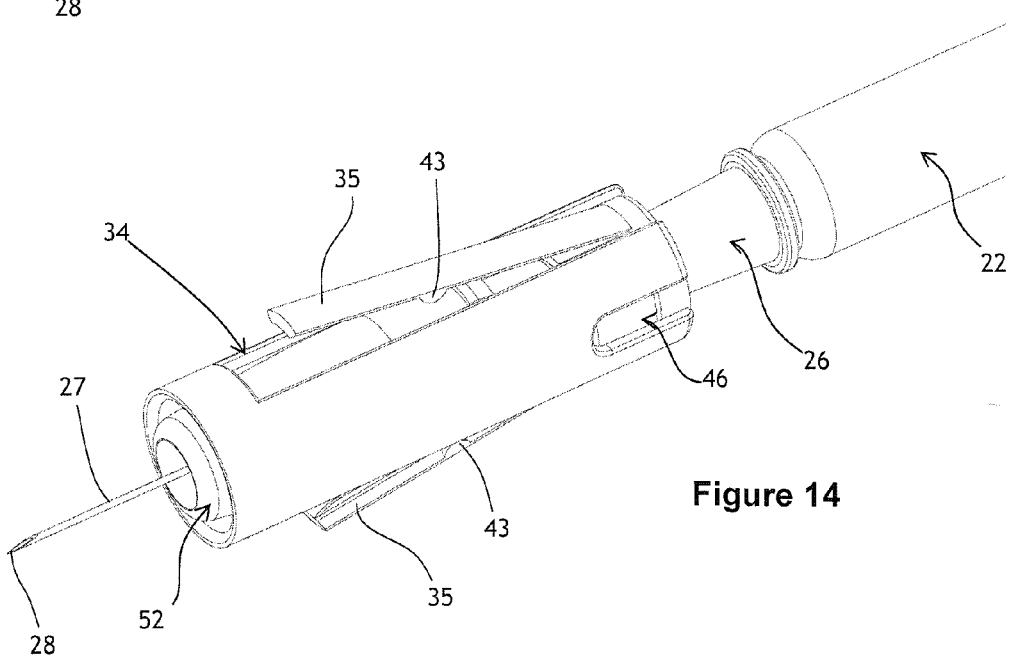
Figure 15:
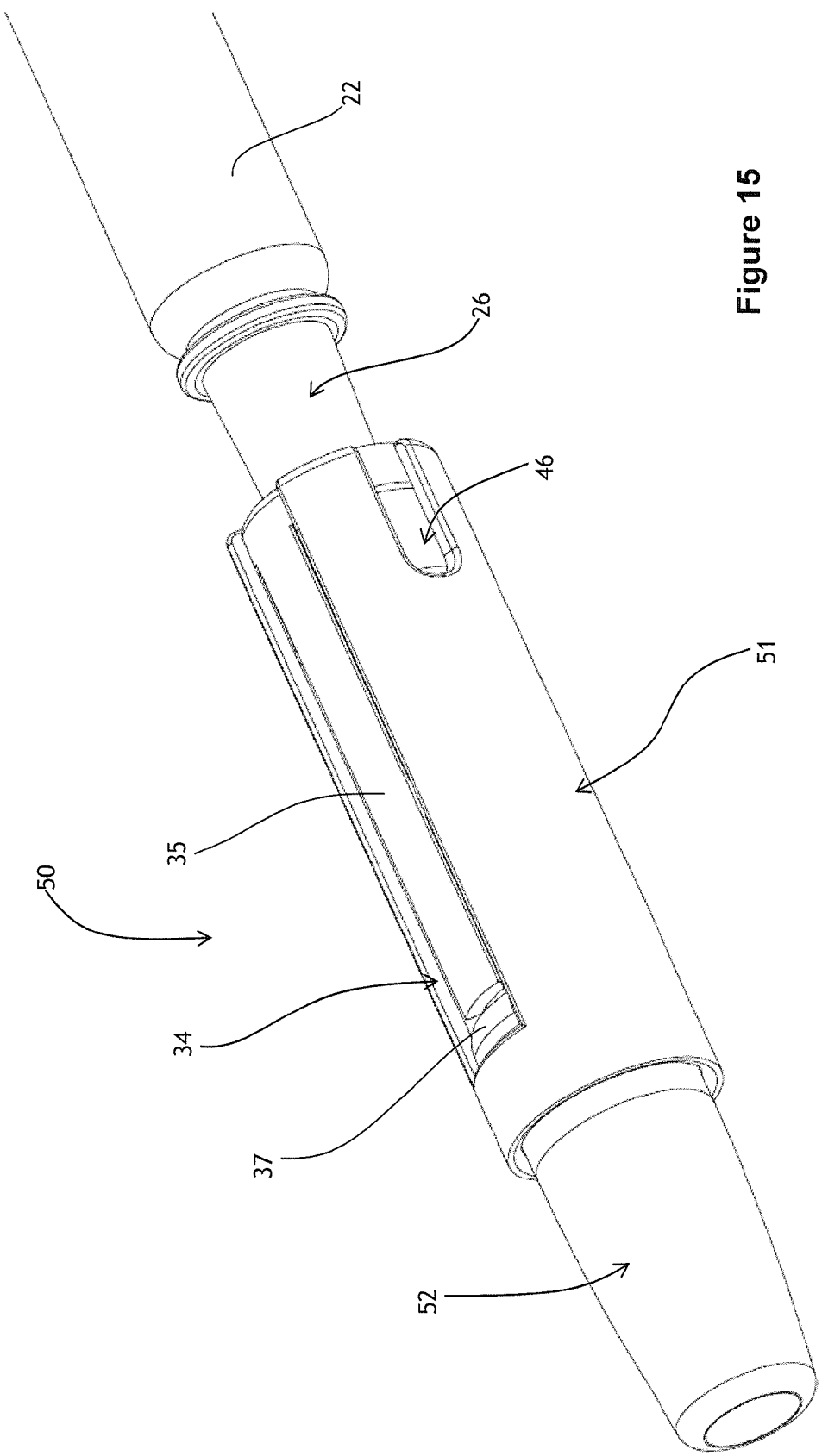
FIG. 15 shows the sleeve returned fully to and blocked in its shielding position.

The syringe, needle and device are advanced to the injection site and the forward end 36 of the sleeve is pressed against the skin. This moves the sleeve rearwardly with respect to the mount 30 so that the protrusions 43 ride up the outer surface of the control member 40, which remains stationary with respect to the mount. As shown in FIG. 4 this resiliently flexes the fingers radially outwardly so that the rearward ends 44 thereof are lifted clear of the shoulder 45 and are brought to bear on forward surfaces 38 of the lugs 37 (FIG. 5). Continued forward movement of the syringe moves the sleeve further rearwardly with respect to mount 30 (FIG. 6) with the inner surfaces of the fingers sliding on the lugs 37 and so being deflected further in the radially outward direction. Eventually, the position is reached where the control member 40 is located at the forward end of the sleeve 33 and the needle projects fully from the forward end of the sleeve (FIG. 7). The fingers are deflected to their greatest extent, storing energy and serving as springs urging the sleeve back to a protecting position.

When in the position of FIG. 7, the injection may be performed by pressing on the plunger 24 so as to dispense the liquid drug out of the syringe through the needle 27. Then, on moving the syringe away from the skin, the axial force exerted on the sleeve by the resilient fingers 35 move the sleeve forwardly with respect to the mount (FIG. 8) while the control member 40 remains at the forward end of the sleeve, maintained there for example by friction. Eventually, the position shown in FIG. 9 is reached where the fingers 35 have returned to their original undeformed condition, free of the mount 30 but the control member 40 remains at the forward end 36 of the sleeve. The sleeve is thus once more in the shielding position with the needle surrounded by the sleeve. If now an attempt is made to move the sleeve rearwardly once more, the rearward ends 44 of the fingers 35 will engage the shoulder 45 of the mount 30 and in view of the respective profiles of the ends of the fingers and that shoulder, increased rearward pressure on the sleeve will serve to strengthen the interengagement of the fingers with the shoulder, so blocking rearward movement of the sleeve.

When in the blocked setting of FIG. 9, the control member will be visible through the windows 46, so showing that the device has been used and must be discarded. Conveniently, this is done by placing the entire assembly of syringe, needle and device in a suitable sharps container. The indication that the device has been used may be enhanced by brightly colouring the control member so enhancing the visibility thereof through the windows 46.

Referring now to FIGS. 11 to 16, there is shown a second embodiment 50 of safety device which operates on broadly the same principles as that of the first embodiment and insofar as is possible, like parts are indicated by like reference characters and will not be described again here. As before, the syringe 22 and the needle together with its needle hub are essentially conventional. In this embodiment, the sleeve 33 (of the first embodiment) is adapted for mounting directly on the needle hub 26 so as to serve as the mount 51 for the device. The mount 30 (of the first embodiment) serves as the sleeve 52 for this second embodiment and so is movable from a fully shielding position (FIG. 12) rearwardly with respect to the needle to a non-shielding position (FIG. 14) at which an injection may be performed. Subsequently, the sleeve 52 moves forwardly to return to its shielding position (FIG. 15) under the action of the fingers 35 which were resiliently deformed radially outwardly in the course of the sleeve 52 moving rearwardly.

The configuration of the fingers 35, the control member 40, the lugs 37 of the sleeve 52 and the windows 46 are all as described above with reference to the first embodiment and have the same functionality. The operation of the device and the sequence thereof will not therefore be described again here. Suffice it to say that in the first embodiment, the mount 30 of the device is carried on the needle hub 26 and the sleeve 33 slides rearwardly over that mount 30. In the second embodiment, the sleeve 33 (of the first embodiment) serves as the mount 51 and is carried on the needle hub; the mount 30 (of the first embodiment) serves as the sleeve 52 and slides rearwardly within the mount 51.

The devices of FIGS. 16 to 21 and FIGS. 22 to 26 are all intended for use with pre-filled syringes having staked-in needles. The device is fitted to a syringe during the manufacture thereof and before the syringe is filled and stoppered with the piston of the syringe plunger. As such, the device is fitted to the syringe instead of a conventional soft or rigid needle cover, during manufacture and before filling. Insofar as is possible, the same reference numbers are used in FIGS. 16 to 21 and FIGS. 22 to 26 as have been used above, to indicate substantially identical or essentially similar parts and those parts will not be described in detail again.

FIGS. 16 to 18 show the device 20 of FIGS. 1 to 10 (i.e. the first embodiment) but fitted with a soft needle cover 55. The open end 56 of the needle cover is cylindrical to be a close fit in the sleeve 33 and the main part 57 of the cover has a tapering form, to its closed end 58. Opposed parallel ribs 59 extend partway along the needle cover from its open end 56 in order to impart sufficient compressive strength to the needle cover, when in use. In a manner well known in the art, a compliant sealant (not shown) is located within the needle cover, to effect a seal to the sharp tip 28 of the needle.

FIG. 16 shows the device 20 assembled with the needle cover 55. The open end 56 bears against the control member 40 and the ribs 59 terminate at the forward end 36 of the sleeve 33, the ribs being disposed at 90° to the fingers 35. The compressive strength of the needle cover is such that the sleeve 33 cannot be moved rearwardly with respect to the mount 30, unless excessive force is applied thereto.

Also shown in FIG. 16 is the syringe 22 having the piston and plunger 24 fitted thereto, though the intention is for the device to be used with a pre-filled syringe, in which case the piston and plunger will not be fitted into the syringe body until filling has been completed, which will be after the device has been fitted to the syringe. The nose of the syringe has been manufactured to provide a first annular ridge 60 adjacent the end of the nose (as is normally the case with a syringe having a staked-in needle) and a second annular ridge 61 between the first ridge 60 and the body of the syringe. The needle is located in a hole formed in the nose of the syringe and is held in place by an adhesive 62.

Fitting the device to the syringe is performed such that the needle cover 55 passes over the first ridge 60 to form an airtight seal therewith and the needle mount 30 rides over and engages behind the second ridge 61, mechanically to hold the device to the syringe. Provided that the syringe and device were sterile before the fitting of the device to the syringe and that the fitting is performed in sterile conditions, the seal made between the cover to the needle tip coupled with the seal between the cover and the first ridge 60 will ensure sterility of the needle is maintained.

Following the fitting of the device to the syringe, the assembly is handled in the usual way for a syringe normally fitted with a needle cover. The assembly is fed to a filling station where the required dose of a medicament is loaded into the syringe which is thereafter stoppered and the plunger fitted such that the assembly is ready for use. This condition is shown in FIG. 17.

When the assembly is to be used, the exposed part of the needle cover 55 is grasped and pulled away from the device 20 as shown in FIG. 18. The cover distorts as required to enable the ribs 59 and cylindrical open end 56 to be pulled through the open end 36 of the sleeve 33. Thereafter, the assembly is as shown in FIGS. 2 to 10 and is used as has been described above.

Though shown with first and second annular ridges 60 and 61 other seal arrangements may be provided on the nose of the syringe, for the needle cover 55. Also, the needle mount 30 may connect to the nose of the syringe other than by being snapped over the second ridge 61. For example, the needle mount may be glued to the syringe or interengaging threads may be provided.

FIGS. 19 to 21 show an arrangement similar to that of FIGS. 16 to 18 but with the device having a rigid needle cover provided with a tamper-evident seal 63. The device 20 itself is again essentially the same as that of the first embodiment, shown in FIGS. 1 to 10.

The rigid needle cover 64 has a tube 65 extending rearwardly from a closed cap 66 having flutes around the periphery thereof. The rearward end 67 of the tube 65 abuts the control member 40 when the cap engages the forward end 36 of the sleeve 33 and an adhesive frangible seal 63 (for example of paper) bridges the junction between the sleeve 33 and cap 66. As with the arrangement of FIGS. 16 to 18, the tube 65 contains a pliable sealant 68 (FIG. 21) for effecting a seal to the needle tip. The mount 30 has a bore configured to effect an airtight seal to a ridge 69 formed around the forward end of the nose of the syringe, either by itself or using some other agent such as an adhesive.

As with the arrangement of FIGS. 16 to 18, the device is assembled to a syringe before the filling thereof. When the assembly has been filled and is ready to use, the tamper-evident seal 63 is broken by grasping the fluted part of the cap and twisting it relative to the sleeve 33 so as to break the seal whereafter the whole needle cover 64 is pulled away from the device (FIG. 20). Once the needle cover has been removed, the assembly is used in the to same manner as has been described above for the first embodiment.

FIG. 22 shows a device similar to that of FIGS. 19 to 21 but for use with a syringe 70 having a standard connector, such as a Luer slip taper, formed on the nose 71. The device 20 is pre-fitted with a needle and hub (not shown) of a standard form, for mounting on the syringe Luer slip connector. In the alternative, the hub of the needle may be formed as the mount 30 for the sleeve 33 and over which the sleeve directly slides when the device is in use. The device is provided with a rigid needle cover 64 as with the previous embodiment, with sealant disposed within the tube (not shown in FIG. 22) of that cover.

The device of FIG. 22 is contained in a sterile package as with conventional needles and is used with the syringe 70 by pressing the syringe into the hub of the needle. The tube 65 of the rigid cover prevents the needle hub (serving as the mount for the device) moving forwardly within the sleeve as the syringe is connected to the needle hub by a pressing and twisting action. Thereafter, following removal of the needle cover 64 the assembly is used as has been described above with reference to FIGS. 19 to 21.

FIGS. 23 to 26 show an arrangement based on the second embodiment of FIGS. 11 to 15. With this arrangement, the mount 73 is cylindrical and wholly contains the syringe body, the mount having at its rearward end a flanged region 74 which holds the rear end of the syringe body. As with the second embodiment, the fingers 75 are connected to the mount 73 adjacent the rear end thereof and engage with lugs 76 provided on a sleeve 77 which slides within the mount 73, and so over the syringe body. A rigid closed package component 78 for the sleeve 77 is fitted thereover and affixed to the mount 73 by a tamper-evident frangible seal 63.

Within the package component 78, there is a structure (not shown) such as a tube projecting internally from the front wall of the component 78, generally co-axial with the safety device, for stripping the needle cover. The structure has formations to grip the needle cover such that after breaking the seal and pulling the package component 78 off the device, the needle cover is stripped off the needle along with the removal of the package component from the safety device, the needle cover remaining in the package component.

Access to the sleeve 77 cannot be gained until the seal 63 is broken and the cover 78 is removed from the assembly (FIG. 24). Thereafter, the assembly of the device and syringe is used much as has been described above in connection with the second embodiment. On offering the forward end 79 of the sleeve 77 to an injection site and then moving the mount 73 (containing the syringe) forwardly, the sleeve retracts within the mount, resiliently deforming the fingers 75 outwardly and simultaneously moving the control member rearwardly. With the full projection of the needle (FIG. 26), the control member 80 becomes visible through the windows 82 of the mount 73 and the fingers are deformed outwardly to their greatest extent. The fingers thus impart a force on the sleeve 77 to move the sleeve back to its initial position, when the assembly is moved away from the injection site. When the sleeve has fully moved back to its initial position and with the control member remaining adjacent the flanged region 74 of the mount, the fingers also revert to their initial unstressed condition and so block subsequent rearward movement of the sleeve. In this way conferred protection is on the used device.

FIGS. 27 and 28 show a package including a device 20 similar to that of the first embodiment, the package including a hollow body 85 closed at one end 86 and open at the other end 87, for receiving the device. A cap 88 fits to the open other end 87 of the body and may be provided with a tamper-evident seal (not shown) similar to that described above. The bore within the body includes opposed ribs 89 which overlie the fingers 90 of the device located within the bore, to prevent activation of the device (i.e. forward movement of the control member from its set position) by bearing on those fingers and preventing radially outward movement thereof.

The device is pre-fitted with a conventional needle having a hub 91 which has a bore forming a part of a conventional syringe connector, such as a Luer slip or Luer lock connector. The hub may fit into the mount 92 of the device, as has been described above with reference to FIGS. 2 to 10. In the alternative, the hub could be specially configured so as to serve as the mount for the device. Sterility may be maintained by fitting the device into the body 85 and closing the other end 87 with cap 88 within a sterile environment, and then fitting a seal around the junction between the cap and body.

The package of FIGS. 27 and 28 is used by twisting the cap off the body, breaking the seal therebetween if one is provided and then a conventional syringe is connected to the exposed hub 91 of the needle. Once fully connected, the syringe is used to pull the device away from the body 85 whereafter the device is set ready for use as has been described in connection with the first embodiment of FIGS. 1 to 10.

As an alternative to the syringe of FIGS. 1 to 10, the arrangement of FIGS. 27 and 28 is particularly suitable for a pre-filled syringe having a needle permanently staked-in to the syringe nose. A soft needle cover (not shown) is fitted to the needle both to maintain sterile conditions for the needle and to seal the sharp tip of the needle and prevent leakage of the pre-filled drug in the syringe. Such a cover may be stripped away by an internal structure (not shown) within the hollow body 85 and projecting rearwardly from the closed end 86. The structure has formations to grip the needle cover so that removal of the hollow body 85 also removes the cover from the needle, readying the device for use.

FIG. 29 shows a modified form of the first embodiment of safety device, intended for use with a so-called pen injector, typically used for self-injection of insulin or other drugs. The pen injector body 95 is arranged for receiving a vial (not shown) of medicament, that vial having a bung at its forward end and which is penetrated by the sharp tip at the rear end of a needle (also not shown) used for performing the injection, that needle being carried within a hub 96. The hub has an internally-threaded bore at the rear end thereof which is arranged to be threaded on to a screw-threaded boss at the forward end of the injector body so that the rear end of the needle is driven rearwardly through the bung of the vial as the connection is completed.

The hub 96 serves as the mount for the safety device 97 which is configured in essentially the same way as that of the first embodiment. Thus, the device has a sleeve 98 slidably mounted on the hub 96 and has a pair of opposed resiliently deformable fingers 99 connected to the sleeve at the forward end thereof. The sleeve is retained on the hub by virtue of lugs 100 projecting through apertures 101 formed in the sleeve, the lugs also providing a sliding surface for the fingers as the sleeve is moved rearwardly. A control member (not shown) is located within the sleeve for sliding movement from an initial set position adjacent the hub 96 to a further position adjacent the forward end of the sleeve, when the sleeve has been slid rearwardly.

It will thus be appreciated that the device of FIG. 29 is essentially the same as that of the first embodiment and operates in the same manner; as such, it will not be described further here.

Figure 30:
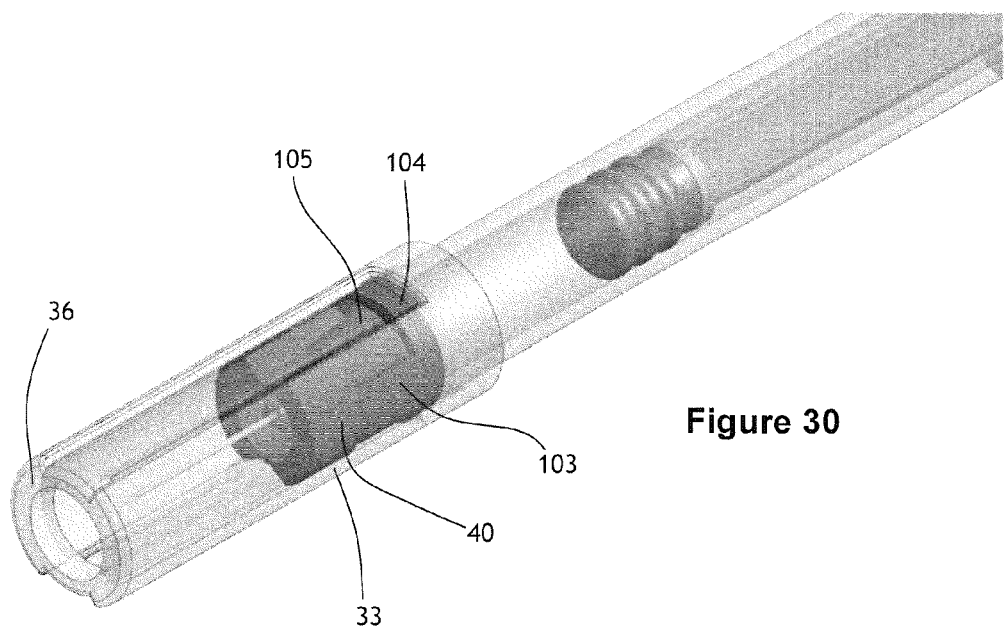
Figure 31:
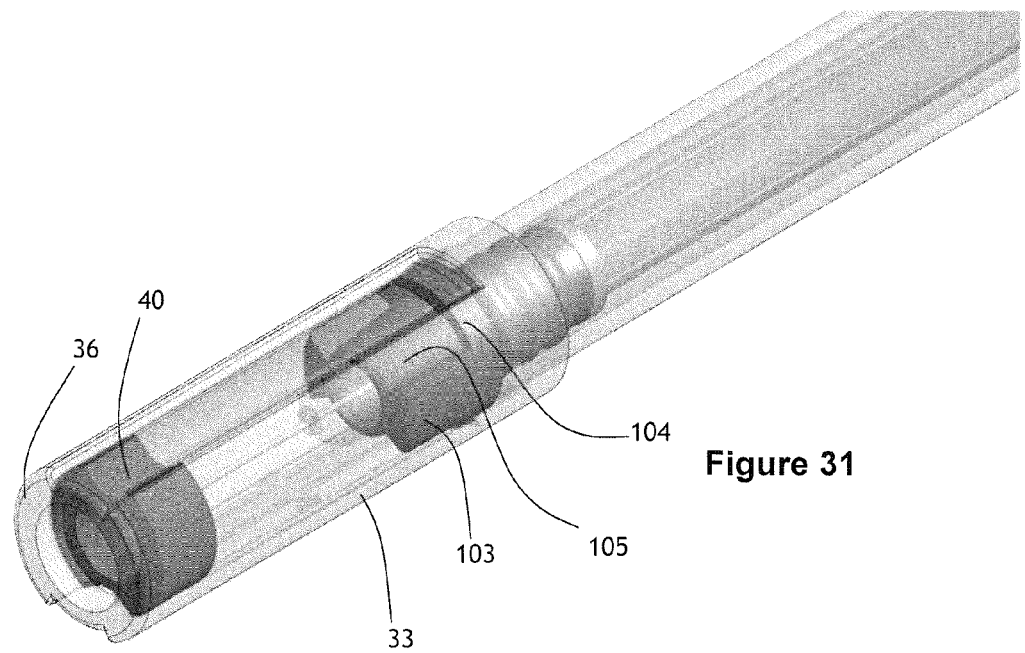

FIGS. 30 and 31 show a modified form of the first embodiment described with reference to FIGS. 1 to 10. In the device of FIGS. 30 and 31, the sleeve 33 is moulded from a transparent plastics material and the windows 46 are omitted. The control member 40 is moulded from a brightly coloured material (as in the first embodiment) but so too is the mount 103. As compared to the first embodiment, the mount 103 has a slightly different configuration in that no separate boss is provided at the forward end of the mount and the cylindrical surface 104 has opposed cut-away regions 105, such that the profile of the forward part of the mount matches that of the control member 40.

The initial setting of the device is shown in FIG. 30 and the location of the control member 40 adjacent the mount 103 is clearly visible through the transparent sleeve 33, indicating that the device has not been used but is ready for use. Following use, as shown in FIG. 31, the control member 40 is disposed at the forward end 36 of the sleeve and the separated brightly coloured mount 103 and control member 40 serve as an indicator to show that the device has been used and the sleeve 33 is blocked against rearward sliding movement.

Figure 32:
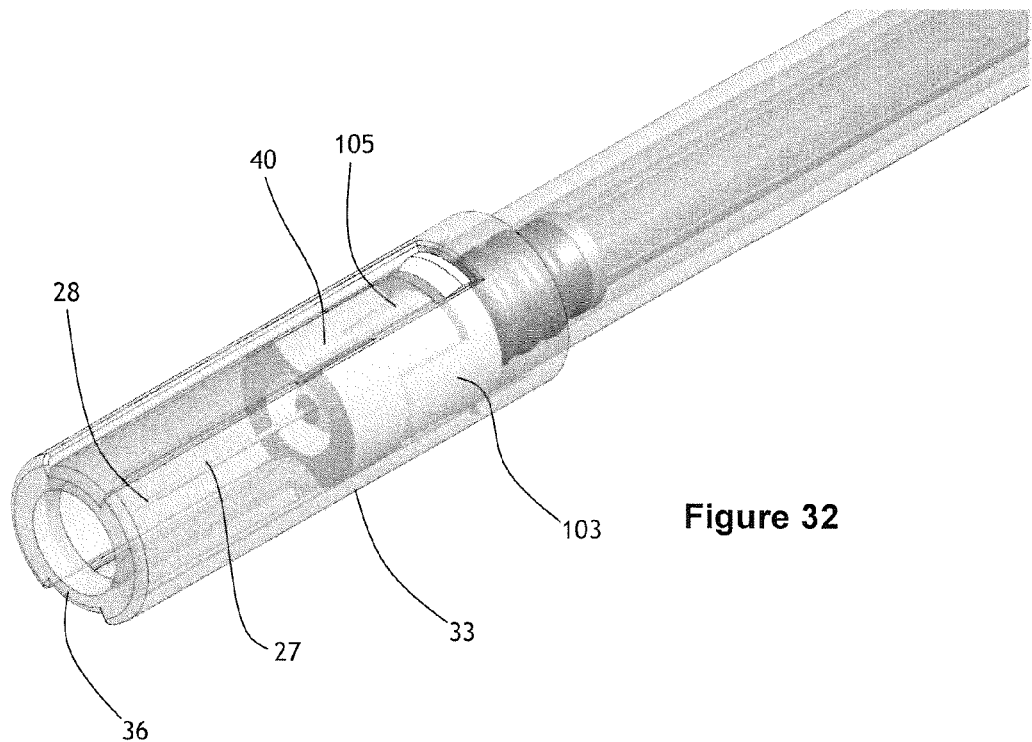
Figure 33:
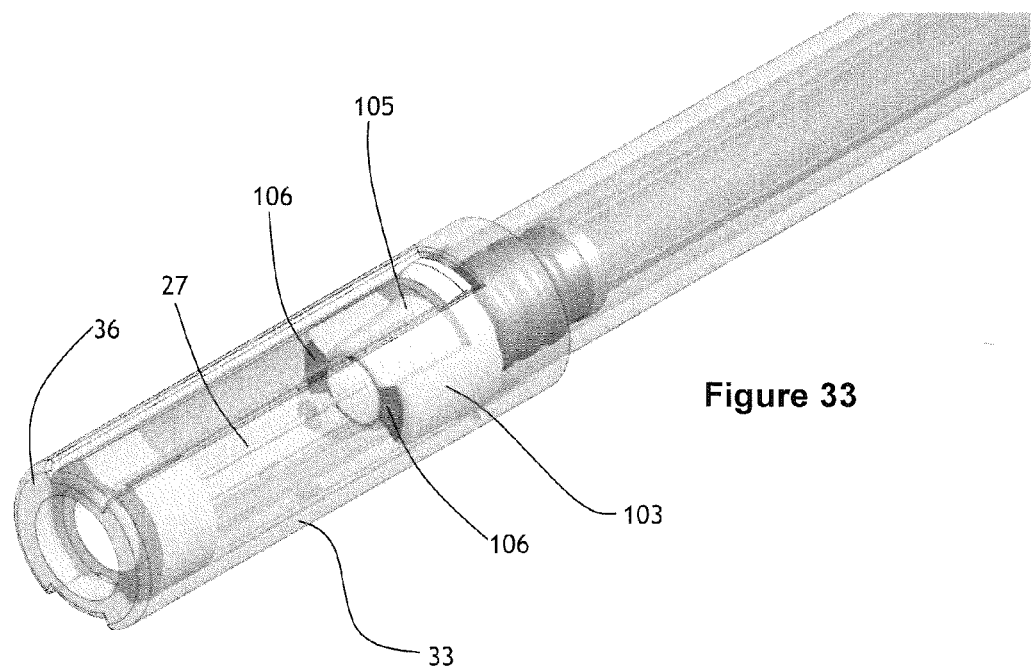

FIGS. 32 and 33 show a modification of the device of FIGS. 30 and 31. Again, the sleeve 33 is moulded from a transparent material but in this embodiment the mount 103 as well as the control member 40 are moulded from a neutral or white coloured plastics material. The forward face 106 of the mount is brightly coloured such that it is readily visible when exposed, through the transparent sleeve.

In the initial setting of the device (FIG. 32), the control member 40 covers the brightly coloured forward face 106 of the mount 103. Following use of the device, as shown in FIG. 33, the control member is located at the forward end 36 of the sleeve 33 thus exposing the forward face 106 of the mount 103 which serves as an indicator to show that the device has been used and the sleeve is blocked against rearward sliding movement.

With all of the embodiments of this invention as described above, the device presents a relatively large diameter bore extending therethrough, within which is, or is to be, located the needle. In view of the large diameter, a collision between the tip of the needle and the bore during assembly of the needle to the device is much less likely than with many known safety devices, so greatly minimising the likelihood of damage to the tip of the needle.

The invention claimed is:

1. A safety device for shielding a medical needle having a sharp tip, which device comprises:
   a needle mount for directly or indirectly supporting a medical needle;
   a needle shielding sleeve for surrounding a supported needle and arranged coaxially with the mount so that a force applied to the sleeve slides the sleeve relative to the mount from a needle shielding position towards a non-shielding position whereat at least the tip of the needle is exposed beyond the sleeve;
   an abutment surface and a sliding surface provided on either one of said needle shielding sleeve or said needle mount;
   a radially deformable resilient finger provided on the other of said needle shielding sleeve and said needle mount, and having a part in radial alignment with the abutment surface when the finger is undeformed to block movement of the sleeve from said needle shielding position; and
   a control member having an outer surface and arranged coaxially with the needle shielding sleeve and the needle mount and slidably displaceable from a set position with respect thereto the arrangement of the control member being such that initial movement of the sleeve towards a non-shielding position slidably displaces the control member from said set position and causes relative movement between the finger and the control member, the inner surface of the finger riding up the outer surface of the control member to radially deform the finger and move said part thereof out of radial alignment with the abutment surface thereby to allow the sleeve to move to a non-shielding position and bring the inner surface of the finger into contact with the sliding surface, and continued movement of the sleeve slides the inner surface of the finger along the sliding, surface to increase the radial deformation of the finger and store energy therein for returning the sleeve to a needle shielding position whereat the finger is undeformed and said part is in radial alignment with the abutment surface, thereby to block movement of the sleeve towards a non-shielding positiom. consequent upon the displacement of the control member from the set position.

2. A safety device as claimed in claim 1, wherein the mount is of a smaller diameter than the sleeve such that the sleeve slides over the mount, and the finger is carried by the sleeve to project rearwardly for contacting the mount.

3. A safety device as claimed in claim 1, wherein the mount is cylindrical and defines a bore in which. the sleeve is slidably mounted, and the finger is carried by the mount to project forwardly for contacting the sleeve.

4. A safety device as claimed in claim 1, wherein the needle mount has a bore for receiving a needle hub and said hub has a medical needle permanently affixed thereto so as to project forwardly therefrom.

5. A safety device as claimed in claim 1, wherein a medical needle is permanently affixed to the mount so as to project forwardly therefrom.

6. A safety device as claimed in claim 4, wherein the needle hub comprises a part of a syringe, the medical needle is permanently affixed to said part to project forwardly from the syringe, and said part is received in the bore of the mount.

7. A safety device as claimed in claim 1, wherein the finger has one and other ends, said one end of the finger being mounted on said one of the needle shielding sleeve and the needle mount, and said part of the finger is disposed at or adjacent said other end of the finger for engaging said abutment surface when the finger is in its undeformed condition.

8. A safety device as claimed in claim 7, wherein said abutment surface comprises a shoulder formed on said other of the sleeve and mount, between larger and smaller diameter parts thereof.

9. A safety device as claimed in claim 1, wherein the sliding surface of said other of the sleeve and the mount is defined by an upstanding lug and the finger has a radially inner face which slides thereon.

10. A safety device as claimed, in claim 1 wherein the control member is slidably carried within the larger diameter of the sleeve and mount, and is held against rotation with respect thereto.

11. A safety device as claimed in claim 1, wherein the other of the sleeve and mount supports a plurality of fingers spaced circumferentially therearound.

12. A safety device as claimed in claim 1, wherein the control member serves as an indicator to show whether the device is ready for use or has been used and the sleeve is blocked against sliding movement with respect to the mount.

13. A safety device as claimed in claim 12, wherein the control member is of a colour which contrasts with that of the sleeve and mount.

14. A safety device as claimed in claim 12, wherein a window is provided in the coaxial arrangement of sleeve and mount within which the control member is slidably carried at the axial position to which the control member is moved when the sleeve is in its non-shielding position, whereby the control member may be observed through that window.

15. A safety device as claimed in claim 12, wherein at least one of the coaxial arrangement of sleeve and mount is of a translucent material whereby the position of the control member therewithin may be observed.

16. A safety needle assembly comprising a safety deice as claimed in claim 1 in combination with a medical needle housed within the device and shielded by the sleeve when in its shielding position.

17. An injection device comprisinu a safety needle assembly as claimed in claim 16 in combination with a syringe or injector arranged to co-operate with the assembly to permit the performance of a medical procedure with the medical needle, passive safety being imparted to the sharp tip of the needle by said safety needle assembly.

* * * * *